【12】 United States Patent
Pulst

US007446239B2

(10) Patent No.: US 7,446,239 B2
(45) Date of Patent: Nov. 4, 2008

(54) SCA2 KNOCKOUT ANIMAL AND METHODS OF USE

(75) Inventor: Stefan M. Pulst, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 548 days.

(21) Appl. No.: 10/141,541

(22) Filed: May 7, 2002

(65) Prior Publication Data

US 2003/0167495 A1    Sep. 4, 2003

Related U.S. Application Data

(60) Provisional application No. 60/289,231, filed on May 7, 2001.

(51) Int. Cl.
*A01K 67/027*  (2006.01)
*A01K 67/00*   (2006.01)
*A01K 67/033*  (2006.01)

(52) U.S. Cl. ............................. 800/18; 800/13; 800/14

(58) Field of Classification Search ..................... 800/8, 800/9, 13, 14, 18
See application file for complete search history.

(56) References Cited

U.S. PATENT DOCUMENTS

| 5,175,384 | A | 12/1992 | Krimpenfort et al. ........... 800/2 |
| 5,602,299 | A | 2/1997 | Lazzarini ........................ 800/2 |
| 5,859,311 | A | 1/1999 | Albers et al. .................... 800/2 |
| 6,037,521 | A | 3/2000 | Sato et al. ...................... 800/18 |
| 6,066,778 | A | 5/2000 | Ginsburg et al. ............... 800/2 |
| 6,194,171 | B1 | 2/2001 | Pulst et al. ................... 435/69.1 |
| 6,251,589 | B1 | 6/2001 | Tsuji et al. .................... 435/6 |
| 6,355,690 | B1 | 3/2002 | Tsuji .......................... 514/706 |
| 6,515,197 | B1 * | 2/2003 | Pulst et al. .................... 800/18 |

FOREIGN PATENT DOCUMENTS

| WO | WO 97/42314 | 11/1997 |
| WO | WO 00/12710 | 3/2000 |

OTHER PUBLICATIONS

Bradley et al. (1992) Modifying the mouse: Design and desire. Bio/Technology 10: 534-539.*
Campbell and Wilmut (1997) Totipotency and multipotentiality of cultured cells: Applications and progress. Theriogenology 47: 63-72.*
Doetschman, T. (1999) Interpretation of phenotype in genetically engineered mice. Laboratory Animal Science 49(2): 137-143.*
Donehower et al. (1995) Effects of genetic background on tumorigenesis in p53-deficient mice. Molecular Carcinogenesis 14: 16-22.*
Huynh et al. (Sep. 2000) Nuclear localization or inclusion body formation of ataxin-2 are not necessary for SCA2 pathogenesis in mouse or human. Nature Genetics 26: 44-50.*
Jacks et al. (1992) Effects of an Rb mutation in the mouse. Nature 359: 295-300.*
Jaenisch et al. (1988) Transgenic Animals. Science 240: 1468-1474.*
Kuehn et al. (1987) A potential animal model for Lesch-Nyhan syndrome through introduction of HPRT mutations into mice. Nature 326: 295-298.*
Moens et al. (1993) Defects in heart and lung development in compound heterozygotes for two different targeted mutations at the N-myc locus. Development 119: 485-499.*
Mullins et al. (1996) Transgenesis in the rate and larger mammals. J. Clin. Invest. 97(7): 1557-1560.*
Petridou et al. (2003) Heterogeneous inducible mammary-specific expression of JAB/SOCS1 in lactating transgenic mice is associated with no obvious phenotype, even at the cellular level. Transgenic Research 12: 693-706.*
Sigmund, CD (2000) Viewpoint: Are studies in genetically altered mice out of control? Arterioscler. Thromb. Vasc. Biol. 20: 1425-1429.*
Burright et al., "SCA1 Transgenic Mice: A Model for Neurodegeneration Caused by an Expanded CAG Trinucleotide Repeat," *Cell* 82:937-948 (1995).
Cha et al., "Altered neurotransmitter receptor expression in transgenic mouse models of Huntington's disease," *Phil. Trans. R. Soc. Lond. B*. 354:981-989 (1999).
Chai et al., "Evidence for proteasome involvement in polyglutamine disease: localization to nuclear inclusions in SCA3/MJD and suppression of polyglutamine aggregation in vitro," *Hum. Mol. Genet*. 8:673-682 (1999).
Clark et al., "Purkinje Cell Expression of a Mutant Allele of *SCA1* in Transgenic Mice Leads to Disparate Effects on Motor Behaviors, Followed by a Progressive Cerebellar Dysfunction and Histological Alterations," *J. Neurosci*. 17:7385-7395 (1997).
Cummings et al., "Mutation of Eg-AP Ubiquitin Ligase Reduces Nuclear Inclusion Frequency While Accelerating Polyglutamine-Induced Pathology in *SCA1* Mice," *Neuron* 24:879-892 (1999).
Cummings et al., "Chaperone suppression of aggregation and altered subcellular proteasome localization imply protein misfolding in SCA1," *Nature Genet*. 19:148-154 (1998).
David et al., "Cloning of the SCA7 gene reveals a highly unstable CAG repeat expansion," *Nature Genet*. 17:65-70 (1997).
Davies et al., "Formation of Neuronal Intranuclear Inclusions Underlies the Neurological Dysfunction in Mice Transgenic for the HD Mutation," *Cell* 90:537-548 (1997).

(Continued)

*Primary Examiner*—Anne-Marie Falk
(74) *Attorney, Agent, or Firm*—McDermott Will & Emery LLP

(57) ABSTRACT

The invention provides a mutant non-human mammal having a disrupted SCA2 gene, in particular, a mutant mouse having a disrupted SCA2 gene. The invention also provides methods of identifying a therapeutic agent for use in treating obesity or memory impairment by administering a compound to the mutant non-human mammal having a disrupted SCA2 gene and screening said mutant non-human mammal for reduced obesity, thereby identifying a therapeutic agent for use in treating obesity.

17 Claims, 4 Drawing Sheets

OTHER PUBLICATIONS

GenBank: Accession No. AA002843.
GenBank: Accession No. AF041472.
GenBank: Accession No. AF223576.
GenBank: Accession No. AK006480.
GenBank: Accession No. AK008433.
GenBank: Accession No. AK012370.
GenBank: Accession No. Aw258842.
GenBank: Accession No. L04961.
GenBank: Accession No. NM_024188.
GenBank: Accession No. NM_133362.
GenBank: Accession No. U70323.
GenBank: Accession No. U70670.
Gutekunst et al., "Nuclear and Neuropil Aggregates in Huntington's Disease: Relationship to Neuropathology," *J. Neurosci.* 19:2522-2534 (1999).
Hodgson et al., "A YAC Mouse Model for Huntington's Disease with Full-Length Mutant Huntingtin, Cytoplasmic Toxocity, and Selective Striatal Neurodegeneration," *Neuron* 23:181-192 (1999).
Hogan et al., *Manipulating the Mouse Embryo: A Laboratory Manual*, Cold Spring Harbor Laboratory (1986).
Holmberg et al., "Spinocerebellar ataxia type 7 (SCA7) : a neurodegenerative disorder with neuronal intranuclear inclusions," *Hum. Mol. Genet.* 7:913-918 (1998).
Huntington's Disease Collaborative Research Group, "A Novel Gene Containing a Trinucleotide Repeat That Is Expanded and Unstable on Huntington's Disease Chromosomes," *Cell* 72:971-983 (1993).
Huynh et al., "Nuclear localization or inclusion body formation of ataxin-2 are not necessary for SCA2 pathogenesis in mouse or human," *Nature Genet.* 26:44-50 (2000).
Huynh et al., "Expression of Ataxin-2 in Brains from Normal Individuals and Patients with Alzheimer's Disease and Spinocerebellar Ataxia 2," *Ann. Neurology* 45:232-241 (1999).
Igarashi et al., "Suppression of aggregate formation and apoptosis by transglutaminase inhibitors in cells expressing truncated DRPLA protein with an expanded polyglutamine stretch," *Nature Genet.* 18:111-117 (1998).
Ikeda et al., "Expanded polyglutamine in the Machado-Joseph disease protein induces cell death in vitro and in vivo," *Nature Genet.* 13:196-202 (1999).
Imbert et al., "Cloning of the gene for spinocerebellar ataxia 2 reveals a locus with high sensitivity to expanded CAG/glutamine repeats," *Nature Genet.* 14:285-291 (1996).
Ishikawa et al., "Abundant expression and cytoplasmic aggregation of α1A voltage-dependent calcium channel protein associated with neurodegeneration in spinocerebellar ataxia type 6," *Hum. Mol. Genet.* 8:1185-1193 (1999).
Kawaguchi et al., "CAG expansions in a novel gene for Machado-Joseph disease at chromosome 14q32.1," *Nature Genet.* 8:221-228 (1994).
Kiehl et al., "The Ortholog of Human Ataxin-2 is Essential for Early Embryonic Patterning in *C. elegans*," *J. Mol. Neurosci.* 15:231-41 (2000).
Kim et al., "Mutant Huntingtin Expression in Clonal Striatal Cells: Dissociation of Inclusion Formation and Neuronal Survival by Caspase Inhibition," *J. Neurosci.* 19:964-973 (1999).
Klement et al., "Ataxin-1 Nuclear Localization and Aggregation: Role in Polyglutamine-Induced Disease in SCA1 Transgenic Mice," *Cell* 95:41-53 (1998).
Koeppen A., "The Purkinje Cell and its Afferents in Human Hereditary Ataxia," *Neuropathol. Exp. Neurol.* 50:505-514 (1991).
Koide et al., "Unstable expansion of CAG repeat in hereditary dentatorubral-pallidoluysian atrophy (DRPLA)," *Nature Genet.* 6:9-13 (1994).
Koyano et al., "Neuronal intranuclear inclusions in spinocerebellar ataxia type 2: triple-labeling immunofluorescent study," *Neurosci. Lett.* 273: 117-120 (1999).
Kozlov et al., "Structure and function of the C-terminal PABC domain of human poly (A) -binding protein," *Proc. Natl. Acad. Sci. USA* 98:4409-13 (2001).

Kuemmerle et al., "Huntington Aggregates May Not Predict Neuronal Death in Huntington's Disease," *Annals of Neurology* 46:842-849 (1999).
La Spada et al., "Androgen receptor gene mutations in X-linked spinal and bulbar muscular atrophy," *Nature* 352:77-79 (1991).
Lippa et al., "Lewy Bodies Contain Altered α-Synuclein in Brains of Many Familial Alzheimer's Disease Patients with Mutations in Presenilin and Amyloid Precursor Protein Genes," *Am. J. Pathol.* 153:1365-1370 (1998).
Mangiarini et al., "Instability of highly expanded CAG repeats in mice transgenic for the Huntington's disease mutation," *Nature Genet.* 15:197-200 (1997).
Mangiarini et al., "Exon 1 of the *HD* Gene with an Expanded CAG Repeat Is Sufficient to Cause a Progressive Neurological Phenotype in Transgenic Mice," *Cell*, 87:493-506 (1996).
Mangus et al., "Pbplp, a Factor Interacting with *Saccharomyces cerevisiae* Poly (A) -Binding Protein, Regulates Polyadenylation," *Mol. Cell Biol.* 18:7383-96 (1998).
Martindale et al., "Length of huntingtin and its polyglutamine tract influences localization and frequency of intracellular aggregates," *Nature Genet.* 18:150-154 (1998).
Mezey et al., "Alpha synuclein is present in Lewy bodies in sporadic Parkinson's disease," *Mol. Psychiatry* 3:493-499 (1998).
Nechiporuk et al., "The mouse *SCA2* gene: cDNA sequence, alternative splicing and protein expression," *Hum. Mol. Genet.* 7:1301-1309 (1998).
Neuwald et al., "Ataxin-2, global regulators of bacterial gene expression, and spliceosomal snRNP proteins share a conserved domain," *J. Mol. Med.* 76:3-5 (1998).
Orr et al., "Expansion of an unstable trinucleotide CAG repeat in spinocerebellar ataxia type 1," *Nature Genet.* 4:221-226 (1993).
Paulson H., "Human Genetics '99: Trinucleotide Repeats Protein Fate in Neurodegenerative Proteinopathies: Polyglutamine Diseases Join the (Mis) fold," *Am. J. Hum. Genet.* 64:339-345 (1999).
Paulson et al., "Intranuclear Inclusions of Expanded Polyglutamine Protein in Spinocerebellar Ataxia Type 3," *Neuron* 19:333-344 (1997).
Pulst et al., "Moderate expansion of a normally biallelic trinucleotide repeat in spinocerebellar ataxia type 2," *Nature Genet.* 14:269-276 (1996).
Reddy et al., "Behavioural abnormalities and selective neuronal loss in HD transgenic mice expressing mutated full-length *HD* cDNA," *Nature Genet.* 20:198-202 (1998).
Sanchez et al., "Caspase-8 Is Required for Cell Death Induced by Expanded Polyglutamine Repeats," *Neuron* 22:623-633 (1999).
Sanpei et al., "Identification of the spinocerebellar ataxia type 2 gene using a direct identification of repeat expansion and cloning technique, Direct," *Nature Genet.* 14:277-284 (1996).
Saudou et al., "Huntingtin Acts in the Nucleus to Induce Apoptosis but Death Does Not Correlate with the Formation of Intranuclear Inclusions," *Cell* 95:55-66 (1998).
Scherzinger et al., "Huntingtin-Encoded Polyglutamine Expansions Form Amyloid-like Protein Aggregates In Vitro and In Vivo," *Cell* 90:549-558 (1997).
Shibata et al., "A novel protein with RNA-binding motifs interacts with ataxin-2," *Hum. Mol. Genet.* 9:1303-1313 (2000).
Stenoien et al., "Polyglutamine-expanded androgen receptors form aggregates that sequester heat shock proteins, proteasome components and SRC-1, and are suppressed by the HDJ-2 chaperone," *Hum. Mol. Genet.* 8:731-741 (1999).
Trottier et al., "Heterogeneous Intracellular Localization and Expression of Ataxin-3," *Neurobiology of Disease* 5:335-347 (1998).
Vandaele et al., "*Purkinje cell protein-2* regulatory regions and transgene expression in cerebellar compartments," *Genes and Develop.* 5:1136-1148 (1991).
Vig et al., "Reduced immunoreactivity to calcium-binding proteins in Purkinje cells precedes onsets of ataxia in spinocerebellar ataxia-1 transgenic mice," *Neurology* 50:106-113 (1998).
Wellington et al., "Caspase Cleavage of Gene Products Associated with Triplet Expansion Disorders Generates Truncated Fragments Containing the Polyglutamine Tract," *J. Biol. Chem.* 273:9158-9167 (1998).

Zhuchenko et al., "Autosomal dominant cerebellar ataxia (SCA6) associated with small polyglutamine expansions in the $\alpha_{1A}$-voltage-dependent calcium channel," *Nature Genet.*, 15:62-69 (1997).

Kiehl et al, "Knockout models for Ataxin-2 and Ataxin-2-binding-protein: gene function developmental genetics, and clinical relevance," *Neurology* 54: Suppl.3 A464 (2000).

Kiehl et al., "Ataxin-2 deficiency in the mouse: From phenotype to expression profiling," *Neurology* 56:Suppl. 3, A81 (2001).

Shastry, B.S. "Genetic knockouts in mice: an update" *Experientia* 51:1028-1039 (1995).

Shastry, B.S. "Gene disruption in mice: Models of development and disease," *Mol. Cell. Biochem.* 181:163-179 (1998).

* cited by examiner

SCA2 KNOCKOUT ANIMAL AND METHODS OF USE

This application claims benefit of the filing date of U.S. Provisional Application No. 60/289,231, filed May 7, 2001, and is incorporated herein by reference.

BACKGROUND OF THE INVENTION

The present invention relates generally to the field of neurobiology and more specifically to a knockout mouse model.

The hereditary ataxias are a complex group of neurodegenerative disorders characterized by varying abnormalities of balance attributed to dysfunction or pathology of the cerebellum and cerebellar pathways. In many of these disorders, dysfunction or structural abnormalities extend beyond the cerebellum, and can involve basal ganglia function, oculomotor disorders and neuropathy. The dominant spinocerebellar ataxias (SCAs) represent a heterogeneous group of disorders with a prevalence of familial cases of approximately 1 in 100,000.

A variety of genes and phenotypes have been identified to be associated with a family of neurodegenerative diseases, including SCA1, SCA2, Machado-Joseph disease (SCA3), SCA6, SCA7, Huntington disease, spinal bulbar muscular atrophy, and dentatorubral pallidoluysian atrophy. These diseases are associated with the expansion of a polyglutamine (polyQ) tract in the protein encoded by the respective disease genes.

Although the study of normal and diseased human brains can provide important insights into polyQ-associated disease pathogenesis, such observations are limited to the terminal stages of the disease process. Mouse models can circumvent this problem, but many mouse models of human polyQ diseases rely on the use of truncated constructs or very long polyQ tracts to produce neruodegeneration (Ikeda et al., Nature Genet., 13:196-202 (1996); Mangiarini et al., Cell, 87:493-506 (1996); Mangiarini et al., Nature Genet., 15:197-200 (1997); Davies et al., Phil. Trans. R. Soc. Lond. B Biol. Sci., 354:981-989 (1999)). In addition, several polyQ mouse models do not show prominent neuronal loss, a defining feature of human polyQ diseases. Furthermore, it is important to understand the function of the genes associated with these neurodegenerative diseases.

Thus, there exists a need for a non-human animal model for the function of genes associated with neurodegenerative disease and methods of identifying therapeutic agents useful for treating conditions associated with these genes. The present invention satisfies this need and provides related advanatages as well.

SUMMARY OF THE INVENTION

The invention provides a mutant non-human mammal having a disrupted SCA2 gene, in particular, a mutant mouse having a disrupted SCA2 gene. The invention also provides methods of identifying a therapeutic agent for use in treating obesity or memory impairment by administering a compound to the mutant non-human mammal having a disrupted SCA2 gene and screening said mutant non-human mammal for reduced obesity, thereby identifying a therapeutic agent for use in treating obesity.

BRIEF DESCRIPTION OF THE DRAWINGS

FIG. 3A shows immunocytochemistry using SCA2-B antibody indicating highly specific staining of oocytes in primary follicles and little background staining in the ovarian stroma. FIG. 3B shows a 20×magnification of FIG. 3A, which indicates that immunoreactivity is confined to the cytoplasm of the oocyte and the surrounding zona pellucida whereas the nucleus is spared.

DETAILED DESCRIPTION OF THE INVENTION

Figure 1:
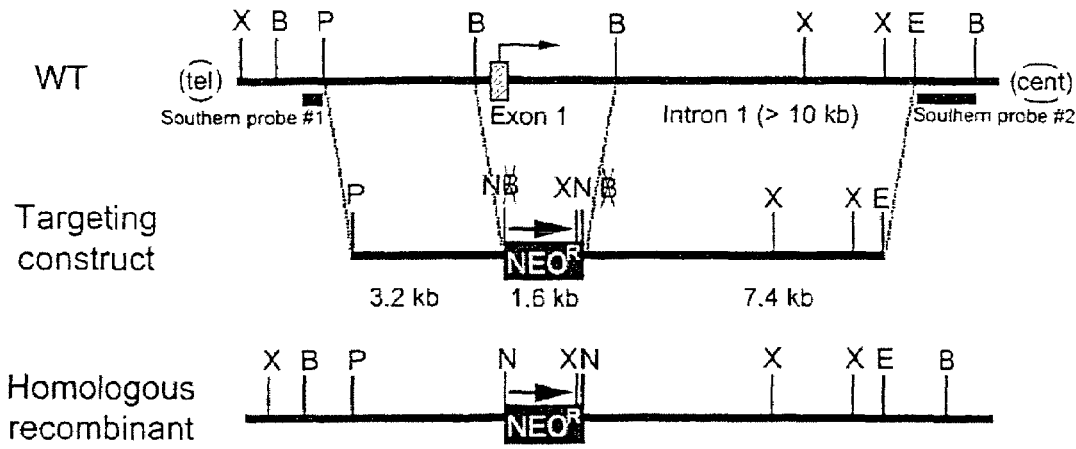
FIG. 1A shows a graphic representation of the SCA2 gene and a targeting strategy.
FIG. 1B shows identification of the targeted allele by southern hybridization.
FIG. 1C shows the ataxin-2 amino acid sequence.
Figure 1:
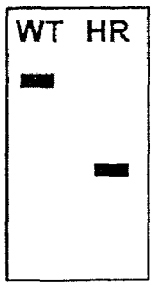
Figure 1:
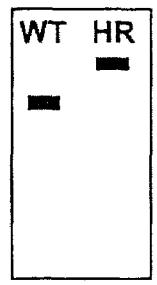
Figure 1:
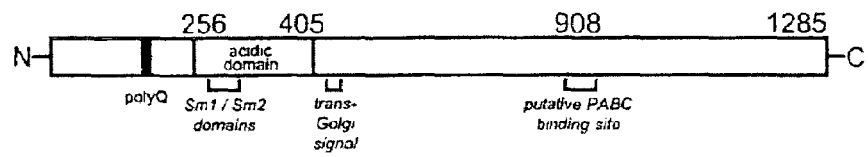

The invention provides a mutant non-human mammal having a disrupted SCA2 gene, in particular, a SCA2 knockout mouse. The SCA2 mutant knockout exhibits obesity as an adult and impaired memory function. The mutant non-human mammal having a disrupted SCA2 gene is useful for identifying the function of ataxin-2, the polypeptide encoded by the SCA2 gene, as well as therapeutic agents for use in treating obesity or memory impairment.

Spinocerebellar Ataxia Type 2 (SCA2) is an autosomal dominant neurodegenerative disease that is caused by expansion of an unstable CAG repeat (Pulst et al., Nature Genet., 14:269-276 (1996); Sanpei et al., Nature Genet., 14:277-284 (1996); Imbert et al., Nature Genet., 14:285-291 (1996). Ataxin-2, the gene product of the SCA2 gene, is a protein of 1312 aa residues having a molecular weight of 120 kDa. Most normal alleles contain 22 or 23 CAG repeats that code for glutamine, flanked by a region of proline and serine rich domains, whereas disease alleles range from 34 to 64 CAG repeats.

The mouse homolog of ataxin-2 is 91% identical and 92% similar to the human protein at the amino acid level (Nechiporuk et al., Hum. Mol. Genet., 7:1301-1309 (1998)). However, it only contains one glutamine at the site of the human polyQ tract, suggesting that the normal function of ataxin-2 does not depend on the CAG repeat. The homologous genes of many polyQ proteins in nonhuman primates contain CAG repeats, although they are much shorter (Dijan et al., Proc. Natl. Acad. Sci. USA 93:417-421 (1996)). Sequence analysis of cDNA indicates that the gene is highly conserved in 5 different mammalian species and in chicken. Other homologs exist in Drosophila, C. elegans, Xenopus and Arabidopsis. Using RNA interference, it was demonstrated that the C. elegans gene atx-2 has an essential role in early embryonic development (Kiehl et al., J Mol Neurosci., 15:231-241 (2000)). This worm gene is expressed in the nervous system, the intestinal lining, the body wall muscle and the germ line.

Except for an acidic domain spanning aa 256 to 405, ataxin-2 is a highly basic and mostly nonglobular protein. Several functional elements were identified in this well-conserved domain, including the RNA splicing motifs Sm1/Sm2 (Neuwald et al., J. Mol. Med., 76:3-5 (1998)). These are characteristic of Sm proteins, central elements of spliceosomal small ribonucleoproteins (snRNPs), which are thought to involve protein-protein interactions and possibly protein-RNA interactions (Hermann et al., Nucleic Acids Res., 14:2076-2088. (1995)). The ataxin-2 sequence also contains the consensus cleavage site DXXD for apopain at amino acid residues 397-400 (Sanpei et al., *Nature Genet.*, 14:277-284 (1996). Studies on huntingtin (Goldberg et al., *Nature Genet.*, 13:442-449 (1996) indicate that the rate of cleavage by apopain increases with the length of the polyglutamine tract and implicate cleavage products in neurotoxicity. Another putative motif present in the sequence is an ER exit signal.

The search for interacting partners of ataxin-2 using yeast two-hybrid screening led to the discovery of ataxin-2-binding-protein 1 (A2BP1) (Shibata et al., *Hum. Mol. Genet.* 9:1303-13 (2000)), which binds to the C-terminus of ataxin-2. The relationship of these proteins was investigated by co-immunoprecipitation, subcellular fractionation and immunofluorescence (Shibata et al., *supra*) as well as histology in the adult and fetal mouse. Recently, the solution structure of the C-terminus of human poly(A)-binding protein was identified (Kozlov et al., *Proc. Natl. Acad. Sci. USA* 98:4409-4413 (2001)) and a consensus sequence of binding peptides was formulated. Among the proteins matching this consensus were ataxin-2 and A2RP. Interestingly, A2BP1 has striking homology to poly(A)-binding proteins in various organisms (Mangus et al., *Mol. Cell Biol.* 18:7383-96 (1998); Shibata et al., *supra*).

SCA2 mRNA is expressed various tissues of the adult mouse, predominantly in the brain, but also in heart, muscle, intestine, spleen, liver, kidney and lung. In contrast, little or no SCA2 mRNA is found in the human kidney and lung (Pulst et al., *Nature Genet.*, 14:269-276 (1996)). Total RNA extracts of whole mouse embryo contain high levels of SCA2 mRNA, which increases from gestational days 8 to 16 (Nechiporuk et al., *Hum. Mol. Genet.*, 7:1301-1309 (1998)). Three alternative SCA2 mRNA transcripts have been identified.

The protein encoded by the SCA2 gene, referred to as ataxin-2, is strongly expressed in neuronal cells of the adult mouse brain such as large pyramidal neurons and subpopulations of hippocampus, thalamus and hypothalamus (Nechiporuk et al., *supra*), as well as in cerebellar Purkinje cells, the primary site of SCA2 neurodegeneration. Non-neuronal tissues also show high-level expression, in particular heart and skeletal muscle. Ataxin-2 is expressed as early as day 8 of mouse embryogenesis. Tissue expression data on adult and fetal mouse A2BP1 is identical to that of ataxin-2. Between day 8 and 10 of gestation, the proteins are present in heart and mesenchyme, but absent in the primitive nervous system. Starting at day 11, however, there is a rapid increase of both proteins in spinal chord and brain. Ataxin-2 has a cytoplasmic localization in normal brain and is expressed in Purkinje cells and specific groups of brain stem and cortical neurons (Huynh et al., *Ann. Neurol.*, 45:232-241 (1999)). Expression increases with age. The juxtanuclear localization of ataxin-2 and A2BP1 was repeatedly shown in neuronal and non-neuronal cell lines (Huynh et al., *supra*); Shibata et al., *supra*). These studies also demonstrated the colocalization of these proteins with markers of the trans-golgi network.

To elucidate the normal function of ataxin-2, a mouse model was generated with a targeted deletion in the SCA2 gene by homologous recombination, as disclosed herein. Northern blot confirmed the absence of SCA2 transcripts in mice homozygous for the targeted allele and western blot demonstrated the absence of immunoreactive proteins. Despite the widespread expression of ataxin-2 during development, SCA2$^{-/-}$ mice were viable and have no obvious defects or increased morbidity. Detailed macroscopic and microscopic analysis of young wild type (WT) and nullizygous SCA2 knockout (KO) mice showed no major differences. However, older KO animals show marked obesity and exhibited impaired memory.

The present invention provides a mutant non-human mammal comprising a mutant SCA2 gene. As disclosed herein, a "mutant" refers to a genetic change, for example, a mutant form of a nucleic acid or encoded polypeptide means that the nucleic acid contains a genetic modification relative to a parent nucleic acid such as the wild type form of the nucleic acid. Similarly, a "mutant," when used in reference to an animal refers to an animal that has been genetically modified. The genetic modification can be the insertion of a gene, thereby generating a "transgenic" animal. As used herein, a "transgene," when used in reference to a transgenic animal, refers to a gene that is inserted into the germ line of an animal in a manner that ensures its function, replication, and transmission as a normal gene. The genetic modification can also be the deletion or disruption of a gene, thereby generating a "knockout" animal. A "knockout" mutant animal refers to partial or complete suppression of the expression of at least a portion of a protein encoded by an endogenous DNA sequence in a cell. Similarly, a disrupted gene results in complete or partial suppression of expression of the gene.

A mutant animal of the invention can be any non-human mammal such as a mouse. A mutant animal can also be, for example, other non-human mammals such as rat, rabbit, goat, pig, guinea pig, sheep, cow, non-human primate or any non-human mammal. It is understood that mutant animals expressing a SCA2 mutant such as the SCA2 knockout animals, as disclosed herein, or other mutant forms of SCA2 in addition to the ataxin-2 mutant mouse disclosed herein, can be used in methods of the invention.

As used herein, the term "polypeptide" is intended to refer to a peptide or polypeptide of two or more amino acids. The term "polypeptide analog" includes any polypeptide having an amino acid sequence substantially the same as a sequence specifically described herein in which one or more residues have been conservatively substituted with a functionally similar residue and which displays the ability to functionally mimic an ataxin-2 polypeptide, as described herein. A "modification" of an ataxin-2 polypeptide also encompasses conservative substitutions of an ataxin-2 polypeptide amino acid sequence. Conservative substitutions of encoded amino acids include, for example, amino acids that belong within the following groups: (1) non-polar amino acids (Gly, Ala, Val, Leu, and Ile); (2) polar neutral amino acids (Cys, Met, Ser, Thr, Asn, and Gln); (3) polar acidic amino acids (Asp and Glu); (4) polar basic amino acids (Lys, Arg and His); and (5) aromatic amino acids (Phe, Trp, Tyr, and His). Other minor modifications are included within ataxin-2 polypeptides so long as the polypeptide retains some or all of the structural and/or functional characteristics of an ataxin-2 polypeptide. Exemplary structural characteristics include sequence identity or substantial similarity, antibody reactivity, and presence of conserved structural domains such as RNA binding domains or acidic domains.

As with an ataxin-2 polypeptide, the invention also provides a functional derivative of an ataxin-2 polypeptide. The term "functional", when used herein as a modifier of an invention ataxin-2 polypeptide, or polypeptide fragment thereof, refers to a polypeptide that exhibits functional characteristics similar to ataxin-2 polypeptide. Exemplary functional characteristics of ataxin-2 polypeptide include RNA binding, transport of molecules, or exhibiting a potential neurodegenerative phenotype based on the size of the polyglutamine tract, that is, an ataxin-2 polypeptide having fewer polyglutamines has a normal phenotype and an ataxin-2 polypeptide having a greater number of polyglutamines has a neurodegenerative phenotype, for example, 32 or greater polyglutamines. One skilled in the art can readily determine whether a polypeptide, or encoding nucleic acid sequence, is substantially the same as a reference sequence by comparing functional characteristics of the encoded polypeptides to a reference ataxin-2 polypeptide.

In regard to the knockout non-human mammals of the invention, it is understood that a knockout can be the disruption of one or more functions of an ataxin-2 polypeptide, as described above, including essentially all of the functions of ataxin-2 in the case of the mutant non-human mammals having a disrupted SCA2 gene, as disclosed herein (see Example I). Thus, a SCA2 knockout non-human mammal can have essentially complete loss of function, as in the case where the ataxin-2 polypeptide is not expressed, or can have partial expression, for example, in the case of a heterozygote.

In one embodiment of the invention mutant mammal, the invention provides a homozygous SCA2 mutant non-human mammal, in which two alleles of the SCA2 gene have been knocked out. In another embodiment, the invention further provides a heterozygous SCA2 mutant non-human mammal, in which only one allele of the SCA2 gene is present. In particular, the invention provides a mutant non-human mammal in which the SCA2 gene has been disrupted by homologous recombination using a DNA construct comprising exon 1 of the SCA2 gene. In a particular embodiment, the invention provides a homozygous SCA2 mutant mouse, in which both endogenous SCA2 alleles have been disrupted. In another embodiment, the invention further provides a heterozygous SCA2 mutant mouse, in which only one of the endogenous SCA2 alleles has been disrupted.

A mutant non-human animal of the invention can exhibit a "mutant SCA2 phenotype." As used herein, the term "mutant SCA2 phenotype" means the observable physiological, neurological and biochemical characteristics of a non-human mammal having a mutant SCA2 gene that causes partial or complete suppression of the expression of an ataxin-2 polypeptide encoded by an endogenous SCA2 gene. A mutant SCA2 phenotype is an outcome of the loss of normal SCA2 gene expression and the corresponding loss of normal patterns of gene expression associated with normal levels of SCA2 gene activity. As described in Example II, the loss of normal SCA2 gene expression in a mutant SCA2 non-human mammal can result in obesity, such as late onset obesity, and memory impairment. As described in Example III, the loss of normal SCA2 gene expression in a mutant SCA2 non-human mammal also can result in altered expression of a variety of genes regulated by SCA2. Exemplary genes having increased expression in a non-human mammal having a mutant SCA2 phenotype are inactive X-specific transcript, erythroid differentiation regulator, nuclear ribonucleoprotein L and EST AW258842. Exemplary genes having decreased expression in a non-human mammal having a mutant SCA2 phenotype are peroxiredoxin-2, 3-oxoacid CoA transferase, stearoyl-CoA-desaturase I, nuclear factor 1-X and EST AA002843.

Therefore, a mutant SCA2 phenotype can include physiological changes, such as obesity, neurological changes, such as memory impairment, and biochemical changes, such as increased or decreased gene expression. Non-human mammals exhibiting a mutant SCA2 phenotype, and cells derived therefrom, are useful in methods of screening to identify compounds effective for treating disorders related to a mutant SCA2 phenotype, such as memory impairment and obesity. Animals exhibiting a mutant SCA2 phenotype, and cells derived therefrom, also are useful for identifying potential drug targets that can be modulated for treating disorders related to a mutant SCA2 phenotype.

Methods for generating a mutant animal having a disrupted SCA2 gene are well known to those skilled in the art as described, for example, in Shastry, *Experientia* 51:1028-1039 (1995); Shastry, *Mol. Cell. Biochem.* 181:163-179 (1998); and U.S. Pat. No. 5,616,491, issued Apr. 1, 1997, U.S. Pat. No. 5,750,826, issued May 12, 1998, and U.S. Pat. No. 5,981,830, issued Nov. 9, 1999. For example, a mutant animal can be generated by introducing into an embryonic stem cell a DNA construct having an appropriate insertion in a gene such that homologous recombination of the introduced gene in the embryonic stem cell results in disruption of the gene.

As disclosed herein, a DNA construct was generated by inserting a selectable marker into exon 1 of the SCA2 gene (see Example I). The DNA construct containing the SCA2 exon 1 insert was introduced into embryonic stem cells, and transfected cells were selected. Introduction of the transfected embryonic stem cells into mouse blastocysts resulted in mice carrying the mutated SCA2 gene in the germline. The invention therefore provides methods for making a SCA2 mutant mouse of the invention, in particular, methods for making a SCA2 knockout mouse.

Animal model systems useful for determining the physiological role of the SCA2 gene encoded polypeptide ataxin-2 are also provided and are produced by creating transgenic animals in which the expression of ataxin-2 is altered using a variety of techniques. Examples of such techniques include the insertion of normal or mutant versions of nucleic acids encoding an ataxin-2 polypeptide by microinjection, retroviral infection or other means well known to those skilled in the art, into appropriate fertilized embryos to produce a transgenic animal. (See, for example, Hogan et al., *Manipulating the Mouse Embryo: A Laboratory Manual* (Cold Spring Harbor Laboratory, (1986), and U.S. Pat. Nos. 5,616,491 and 5,750,826).

The present invention provides mutant non-human mammals that have the SCA2 gene knocked out in all their cells. The invention additionally provides animals that in which the knockout of SCA2 occurs in some, but not all their cells, that is, mosaic animals. Furthermore, a SCA2 mutant non-human mammal of the invention having a disrupted SCA2 gene can be crossed with other SCA2 mutant mammals, including a SCA2 transgene, if desired.

The invention additionally provides a DNA construct comprising exon 1 of a SCA2 gene into which a selectable marker sequence has been inserted. As used herein, the term "DNA construct" refers to specific arrangement of genetic elements in a DNA molecule. A DNA construct of the invention will generally contain a sequence homologous to a portion of gene of interest, for example, SCA2. When used to disrupt the expression of an endogenous gene in an animal by homologous recombination, the homologous sequence can be chosen from any genomic sequence so long as recombination of the endogenous gene with the homologous region in the DNA construct leads to disruption of the endogenous gene. In particular, the homologous sequence can contain an exon. A partial nucleotide sequence of mouse SCA2 (GenBank accession number U70670) is referenced as SEQ ID NO:1, while the encoded partial amino acid sequence is referenced as SEQ ID NO:2. A full length nucleotide sequence of mouse SCA2 (GenBank accession number AF041472) is referenced as SEQ ID NO:3, while the encoded amino acid sequence is referenced as SEQ ID NO:4. The nucleotide sequence of human SCA2 (GenBank accession number U70323) is referenced as SEQ ID NO:5, while the encoded amino acid sequence is referenced as SEQ ID NO:6.

In a DNA construct of the invention, the nucleic acid sequence used as the knockout construct is typically comprised of DNA from some portion of the gene, for example, exon sequence, intron sequence and/or promoter sequence, and a marker sequence used to detect the presence of the DNA construct in a cell. The DNA construct is inserted into a cell and integrates with the genomic DNA of the cell in such a position so as to prevent or interrupt transcription of the native DNA sequence. Such insertion usually occurs by homologous recombination, in which regions of the DNA construct that are homologous to endogenous DNA sequences hybridize to each other when the DNA construct is inserted into the cell and recombine so that the DNA construct is incorporated into the corresponding position of the endogenous DNA. The DNA construct sequence can comprise a full or partial sequence of one or more exons and/or introns of the gene to be suppressed, a full or partial promoter sequence of the gene to be suppressed, or combinations thereof.

When used to disrupt the expression of an endogenous gene in an animal, the DNA construct will generally contain an insert in the homologous region. The insert can be, for example, a selectable marker. As used herein, a "selectable marker" refers to a genetic element that provides a selectable phenotype to a cell in which the selectable marker has been introduced. A selectable marker is generally a gene whose gene product provides resistance to an agent that inhibits cell growth or kills a cell. A variety of selectable markers can be used in the DNA constructs of the invention, including, for example, Neo, Hyg, hisD, Gpt and Ble genes, as described, for example in Ausubel et al. (*Current Protocols in Molecular Biology* (Supplement 47), John Wiley & Sons, New York (1999) and U.S. Pat. No. 5,981,830). Drugs useful for selecting for the presence of a selectable marker includes, for example, G418 for Neo, hygromycin for Hyg, histidinol for hisD, xanthine for Gpt, and bleomycin for Ble (see Ausubel et al., *supra*, (1999); U.S. Pat. No. 5,981,830). DNA constructs of the invention can incorporate a positive selectable marker, a negative selectable marker, or both (see, for example, U.S. Pat. No. 5,981,830).

DNA constructs of the invention can be incorporated into vectors for propagation or transfection into appropriate cells, for example, embryonic stem cells. One skilled in the art can select a vector based on desired properties, for example, for production of a vector in a particular cell such as a mammalian cell or a bacterial cell. If desired, the DNA constructs can be engineered to be operably linked to appropriate expression elements such as promoters and/or enhancers to allow expression of a genetic element in the DNA construct in an appropriate cell or tissue.

The invention additionally provides an embryonic stem cell comprising a DNA construct of the invention. As used herein, an "embryonic stem cell" is pluripotent stem cell derived from an embryo of a cognate organism for which introduction of a transgene is desired. In particular, the invention provides an embryonic stem cell comprising a DNA construct comprising a homologous region of SCA2, for example, exon 1 of SCA2 into which a selectable marker has been inserted. Methods of using embryonic stem cells to generate a mutant mouse having a disrupted gene are well known to those skilled in the art (see, for example, U.S. Pat. Nos. 5,616,491 and 5,750,826).

For generation of a mutant mouse, embryonic stem cells are obtained from a mouse or other suitable non-human mammal. Alternatively, an appropriate embryonic stem cell line can be used to introduce a DNA construct of the invention.

The invention further provides an isolated mouse cell containing a DNA construct of the invention. The DNA construct can be introduced into a cell by any of the well known transfection methods (Sambrook et al., *Molecular Cloning: A Laboratory Manual*, 2nd ed., Cold Spring Harbor Press, Plainview, N.Y. (1989); Ausubel et al., *supra*, (1999). Alternatively, the mouse cell can be obtained by isolating a cell from a mutant mouse of the invention and establishing primary cultures. Thus, the invention provides a cell isolated from a SCA2 mutant non-human mammal, such as a mouse. The cells can be obtained from a homozygous SCA2 mutant non-human mammal, such as a mouse, or a heterozygous SCA2 mutant non-human mammal.

The SCA2 mutant non-human mammal of the invention can be advantageously used to, screen for therapeutic agents that can be used to treat obesity or memory impairment. For example, SCA2 mutant knockout mice had increased obesity in adults (see Example II). The invention thus provides a method of identifying a therapeutic agent for use in treating obesity by administering a compound to a SCA2 mutant non-human mammal having a disrupted SCA2 gene and screening the mutant non-human mammal for reduced obesity, thereby identifying a therapeutic agent for use in treating obesity.

As used herein, "reduced obesity" refers to any decrease in the obesity phenotype of a SCA2 mutant non-human mammal. Such a decrease can-include loss of weight, decreased weight gain, decrease rate of weight gain, or any characteristics associated with obesity. One skilled in the art can readily determine reduced obesity based on well known methods of measuring obesity.

The SCA2 mutant knockout mice also exhibited memory impairment (see Example II). Thus, the invention also provides a method of identifying a therapeutic agent for use in treating memory impairment by administering a compound to a SCA2 mutant non-human mammal having a disrupted SCA2 gene and screening the mutant non-human mammal for reduced memory impairment, thereby identifying a therapeutic agent for use in memory impairment.

As used herein, "reduced memory impairment" refers to any decrease in memory impairment, including improved memory. Memory impairment can be screened with a variety of well known tests for memory useful in a particular organism. Exemplary tests for memory changes include, for example, using a Morris water maze or other methods of testing memory. One skilled in the art can readily determine reduced memory impairment based on improved results of an appropriate measure of memory.

As described in Example III, in addition to exhibiting obesity and memory impairment, SCA2 mutant mice also exhibited altered expression of several genes in comparison to wild type mice. For example, SCA2 knockout mice are characterized by increased expression of inactive X-specific transcript, erythroid differentiation regulator, nuclear ribonucleoprotein L and EST AW258842 and decreased expression of peroxiredoxin-2, 3-oxoacid CoA transferase, stearoyl-CoA desaturase I, nuclear factor 1-X and EST AA002843. The altered expression of each of these genes, as well as other genes having altered expression in a mutant SCA2 non-human mammal, indicates that SCA2 normally regulates the expression of these genes in wild type animals. Thus, inactive X-specific transcript, erythroid differentiation regulator, nuclear ribonucleoprotein L and EST AW258842, peroxiredoxin-2, 3-oxoacid CoA transferase, stearoyl-CoA desaturase I, nuclear factor 1-X and EST AA002843 represent genes that can be modulated in order to reverse, or at least partially reverse, the physiological, neurological and biochemical characteristics of a mutant SCA2 phenotype. For example, restoring a more normal level of expression of a target gene having altered expression in a mutant SCA2 non-human mammal can result in reduced obesity or reduced memory impairment. Therefore, a compound that restores a more normal level of expression to a target gene having altered expression in a mutant SCA2 non-human mammal is a potentially useful therapeutic compound for treatment of obesity, memory impairment and related disorders.

Therefore, the invention provides methods for identifying target genes having altered expression in a mutant SCA2 non-human mammal, as well as methods for identifying a compound that restores a target gene having altered expression in a mutant SCA2 non-human mammal to a more normal level of expression.

The method for identifying a target gene having altered expression in a mutant SCA2 non-human mammal involves comparing the expression of one or more genes in a mutant non-human mammal having a disrupted SCA2 gene with the expression of said one or more genes in a wild type animal to identify a gene having altered expression in said mutant non-human mammal, thereby identifying a target gene having altered expression in a mutant SCA2 non-human mammal.

The methods of the invention for identifying a target gene having altered expression in a mutant SCA2 non-human mammal can involve comparing the expression of one or more genes contained within one or more organs of the mutant SCA2 non-human animal. As shown in Example III, gene expression in the cerebrum, cerebellum, heart and skeletal muscle of mutant SCA2 non-human mammals in comparison to wild type mammals was examined. A variety of other organs, tissues or cells of a mutant SCA2 non-human mammals can be compared to those of wild type animals to determine alterations in gene expression.

The method for identifying a compound that restores a target gene having altered expression in a mutant SCA2 non-human mammal to a more normal level of expression involves (a) contacting a target gene having altered expression in a mutant SCA2 non-human mammal with a test compound; (b) determining expression of said target gene, and (c) identifying a compound that modulates expression of said target gene to a level of expression consistent with a wild type level of expression.

A "more normal level" of expression of a target gene is a level of expression of the target gene that is similar to the level of expression of the target gene in a wild type animal. A test compound that restores a target gene having altered expression in a mutant SCA2 non-human mammal to a more normal level of expression changes the level of expression to at level at least about 50% of the normal level of expression in a wild type non-human mammal, intact cell or cell preparation. For example, a test compound that restores a target gene have reduced expression in a mutant SCA2 non-human mammal to a more normal level of expression does so by increasing the level of expression to a level at least about 50% of the normal level of expression. Likewise, a test compound that restores a target gene having increased expression in a mutant SCA2 non-human mammal to a more normal level of expression does so by decreasing the level of expression to a level at least about 50% of the normal level of expression. For example, a test compound can restore at least about 60%, at least about 70%, at least about 80%, at least about 90%, at least about 95%, at least about 98%, or even essentially about 100% of the normal level of expression in a wild type non-human mammal.

A target gene having altered expression can be contained, for example, in a mutant non-human mammal, in an organ, tissue or cell isolated therefrom, or in a cell preparation in which expression of a target gene can be modulated.

The methods of the invention for screening for a compound that restores a target gene having altered expression in a mutant SCA2 non-human mammal to a more normal level of expression-involve contacting a sample exhibiting altered expression of a target gene characteristic of a mutant SCA2 non-human mammal with a test compound. A test compound can be any substance, molecule, compound, mixture of molecules or compounds, or any other composition which is suspected of being capable of restoring an expression level of a target gene to a more normal level.

A test compound can be a macromolecule, such as biological polymer, including polypeptides, polysaccharides and nucleic acids. Compounds useful as potential therapeutic agents can be generated by methods well known to those skilled in the art, for example, well known methods for producing pluralities of compounds, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422-428 (1998); Tietze et al., *Curr. Biol.*, 2:363-371 (1998); Sofia, *Mol. Divers*. 3:75-94 (1998); Eichler et al., *Med. Res. Rev.* 15:481-496 (1995); and the like. Libraries containing large numbers of natural and synthetic compounds also can be obtained from commercial sources. Combinatorial libraries of molecules can be prepared using well known combinatorial chemistry methods (Gordon et al., *J. Med. Chem.* 37: 1233-1251 (1994); Gordon et al., *J. Med. Chem.* 37: 1385-1401 (1994); Gordon et al., *Acc. Chem. Res.* 29:144-154 (1996); Wilson and Czarnik, eds., *Combinatorial Chemistry: Synthesis and Application*, John Wiley & Sons, New York (1997)).

Additionally, a test compound can be preselected based on a variety of criteria. For example, suitable test compounds having known modulating activity on a pathway suspected to be involved in a mutant SCA2 phenotype can be selected for testing in the screening methods. Alternatively, the test compounds can be selected randomly and tested by the screening methods of the present invention. Test compounds can be administered to the reaction system at a single concentration or, alternatively, at a range of concentrations from about 1 nM to 1 mM.

The number of different test compounds examined using the methods of the invention will depend on the application of the method. It is generally understood that the larger the number of candidate compounds, the greater the likelihood of identifying a compound having the desired activity in a screening assay. The methods can be performed in a single or multiple sample format. Large numbers of compounds can be processed in a high-throughput format which can be automated or semi-automated.

The expression of a target gene, or the modulation of expression of a target gene by a test compound, can be determined by measuring changes in expression. The methods of the invention involve measuring changes in gene expression by determining the amount of mRNA or polypeptide present in a sample. Methods for measuring both mRNA and polypeptide quantity are well known in the art. Methods for measuring mRNA typically involve detecting nucleic acid molecules by specific hybridization with a complementary probe in solution or solid phase formats. Such methods include northern blots, polymerase chain reaction after reverse transcription of RNA (RT-PCR), and nuclease protection. Measurement of a response of a pathway component can be performed using large scale gene expression methods.

Large scale gene expression methods can be advantageously used to measure a large population of expressed genes in an organ, tissue or cell. Examples of methods well known in the art applicable to measuring a change in expression of a population of genes include cDNA sequencing, clone hybridization, differential display, subtractive hybridization, cDNA fragment fingerprinting, serial analysis of gene expression (SAGE), and DNA microarrays. These methods are useful, for example, for identifying differences in gene expression in an organ, tissue or cell of a mutant SCA2 non-human mammal compared to that of a wild type control animal. Example III describes the use of an Affymetrix chip for determining changes in expression in a population of genes in mutant SCA2 mice in comparison to wild type mice. Methods of detecting changes in gene expression can be performed both qualitatively or quantitatively.

A level of protein expression corresponding to a gene expression level also can be determined, if desired. A variety of methods well known in the art can be used to determine protein levels either directly or indirectly. Such methods include immunochemical methods, such as western blotting, ELISA, immunoprecipitation, and RIA, gel electrophoresis methods including one and two-dimensional gels, methods based on protein or peptide chromatographic separation, methods that use protein-fusion reporter constructs and calorimetric readouts, methods based on characterization of actively translated polysomal mRNA, and mass spectrometric detection.

The methods of the invention for identifying a compound that restores a target gene having altered expression in a mutant SCA2 non-human mammal to a more normal level of expression can involve determining an activity of a target gene. The activity of a molecule can be determined using a variety of assays appropriate for the particular target. A detectable function of a target gene can be determined based on known or inferred characteristics of the target gene. For example, the peroxiredoxin-2 gene has a role in reducing oxidative stress, the inactive X-specific transcript (XIST) gene has a role in X-inactivation, and the erythroid differentiation regulator gene has an ubiquitous role in regulating differentiation. Thus, based on known characteristics of these genes, which have modulated expression in a mutant SCA2 non-human mammal, appropriate assays for determining gene function can be determined.

Compounds identified as therapeutic agents by methods of the invention can be administered to an individual, for example, to alleviate a sign or symptom associated obesity, memory impairment, or any phenotype associated with a SCA2 mutant non-human mammal of the invention. One skilled in the art will know or can readily determine the alleviation of a sign or symptom associated with obesity or memory impairment.

If desired, appropriate control animals can be used to corroborate the therapeutic effectiveness of screened compounds. For example, a control animal can be one that is expressing SCA2 such as a wild type animal. Alternatively, a control animal can express a form of an ataxin-2 polypeptide that does not result in a mutant SCA2 phenotype, such as obesity or memory impairment.

For use as a therapeutic agent, the compound can be formulated with a pharmaceutically acceptable carrier to produce a pharmaceutical composition, which can be administered to the individual, which can be a human or other mammal. A pharmaceutically acceptable carrier can be, for example, water, sodium phosphate buffer, phosphate buffered saline, normal saline or Ringer's solution or other physiologically buffered saline, or other solvent or vehicle such as a glycol, glycerol, an oil such as olive oil or an injectable organic ester. A pharmaceutically acceptable carrier can also contain physiologically acceptable compounds that act, for example, to stabilize or increase the absorption of the modulatory compound. One skilled in the art would know that the choice of a pharmaceutically acceptable carrier, including a physiologically acceptable compound, depends, for example, on the route of administration of the composition.

The methods of the invention can advantageously use cells isolated from a homozygous or heterozygous SCA2 mutant non-human mammal for a desired purpose. The methods of the invention can also be used with cells in which the SCA2 gene has been disrupted such as a transfected cell line.

A cell expressing a SCA2 encoding an ataxin-2 polypeptide can be used as an in vitro method to screen compounds as potential therapeutic agents for treating obesity or memory impairment. In such a method, a compound is contacted with a cell having disrupted SCA2 expression, either a transfected cell or a cell derived from a SCA2 mutant non-human mammal, and screened for alterations in a phenotype associated with decreased expression of the SCA2 gene.

The invention further provides a method of identifying a potential therapeutic agent for use in treating obesity or memory impairment. The method includes the steps of contacting a cell containing a DNA construct comprising nucleic acid encoding a mutant ataxin-2 polypeptide with a compound; and screening the cell for improvement of a particular phenotype associated with the mutant ataxin-2 polypeptide, including decreased ataxin-2 expression, thereby identifying a potential therapeutic agent for use in treating an associated phenotype such as obesity or memory impairment. The cell can be a transfected cell expressing the mutant ataxin-2 polypeptide or isolated from a transgenic non-human mammal having nucleated cells containing a disrupted SCA2 gene.

Cells expressing a mutant ataxin-2 polypeptide, including cells having decreased ataxin-2 expression, can be used in a preliminary screen to identify compounds as potential therapeutic agents having activity that alters a phenotype associated with decreased SCA2 expression. As with in vivo screens using SCA2 mutant non-human mammals, an appropriate control cell can be used to compare the results of the screen, for example, a control cell expressing a SCA2 gene such as a wild type cell or a control cell expressing a form of SCA2 that does not exhibit an phenotype associated with SCA2 disruption, such as obesity or memory impairment. The effectiveness of compounds identified by an initial in vitro screen using cells having decreased SCA2 gene expression can be further tested in vivo using the invention SCA2 mutant non-human mammals, if desired. Thus, the invention provides methods of screening a large number of compounds using a cell-based assay, for example, using high throughput screening, as well as methods of further testing compounds as therapeutic agents in an animal model using the SCA2 mutant non-human mammals of the invention.

This study is the first description of a targeted disruption of the mouse SCA2 gene, generated by homologous recombination. The results of this study indicate that the cytoplasmic protein ataxin-2, despite widespread expression at various embryonic and adult stages, does not seem to be essential in development. However, the remarkably high degree of evolutionary conservation with homologs in *Drosophila, Xenopus, C. elegans* (Kiehl et al., 2000) and *Arabidopsis* indicates an important basic cellular function.

The non-essential role of ataxin-2 despite widespread expression in development can possibly be explained by orthologs and mechanisms that may rescue the function. For instance, ataxin-2-related protein (A2RP) on chromosome 16 is 41% similar and 16% identical in amino acid sequence to ataxin-2. Although this indicates considerable divergence from a putative ancestral gene, A2RP might still rescue some of the ataxin-2 function in the knockout. The motifs that are shared between the two are Sm1 and Sm2 RNA splicing motifs, apopain cleavage site, ER exit signal and trans-golgi signal. Both ataxin-2 and A2RP therefore have considerable similarity to the Sm proteins (Neuwald and Koonin, *J. Mol. Med.*, 76:3-5 (1998)). In order for translation of eukaryotic transcripts to occur, newly synthesized mRNAs (pre-mRNAs) are processed by a splicing machinery. Introns are removed by the spliceosome, a large complex made up of small nuclear ribonucleoprotein particles (snRNPs). Numerous SM-like proteins can be identified by sequence comparison. Although their role in mRNA processing and degradation is certain, data on target binding specificity is limited. It can be hypothesized that each SM protein binds to a number of different target RNAs. Because an overlap in these targets is likely, absence of one splicing mechanism can be expected to change the level of certain transcripts without necessarily being fatal to the cell. In addition, compensatory mechanisms by structurally unrelated genes can be involved.

Yeast proteins with considerable sequence similarity to ataxin-2 and A2BP1 are involved in polyadenlyation (Mangus et al., *supra*). In fact, the interaction between yeast PBP1, which is similar to ataxin-2, and Pab1p (similar to A2BP1) plays a key role in the translation machinery. The human counterparts are poly(A) binding protein (PABP) and its interactor PAIP1. They act via eukaryotic initiation factor 4G (eIF4G, Craig et al., *Nature* 392:520-3 (1998)) to initiate translation. A2BP1 has homology to polyadenylate-binding proteins from a wide range of organisms. When the partial structure of human PABP was recently determined (Kozlov et al., *Proc. Natl. Acad. Sci. USA* 98:4409-4413 (2001)), ataxin-2 was identified as a potential binding partner.

When the expression of ataxin-2 and A2bp1 was examined during embryonic development, it became apparent that there is tightly regulated temporal and tissue-specific expression. Previous studies had implicated these proteins in development (Nechiporuk et al., (1998); Kiehl et al., *supra*). Across different tissue types, there was a characteristic immunocytochemistry staining pattern in which only certain subpopulations of cells were labeled. A number of reasons can account for the absence of an overt embryonic phenotype in this knockout. As described above, homologous genes could take over some of the function. If ataxin-2 is indeed a ligand of PABP, then other ligands can have similar and overlapping RNA specificities.

Adult body weight is maintained as a result of energy intake as food calories and expenditure in the form of metabolism and activity. This study showed a significantly increased body weight in adult SCA2(-/-) animals. It is presently unclear whether this is due to metabolic or behavioral factors. Several knockout mouse models with an obese phenotype were shown to have increased feed-efficiency, meaning a higher weight gain per calorie ingested. Recently, the receptors for melanocortin-3 (mc3r, Chen et al., *Nat Genet.* 26::97-102 (2000)) and melanocortin-4 (mc4r, Ste. Marie et al., *Proc Natl Acad Sci USA* 97:12339-44 (2000)) were shown to lead to obesity by two distinct mechanisms. While the mc3 receptor regulates feed efficiency and fat mass, the mc4 receptor is involved in the regulation of food intake and energy expenditure. The phenotype is exacerbated in double knockouts (Cummings et al., *Nat Genet.* 26:8-9 (2000)). The melanocortins are mediators of leptin action, gene product of the ob gene in mice (Zhang et al., *Nature* 372:425-32 (1994)). Leptin-deficient (ob/ob) mice have a complex obesity phenotype of hyperphagia and lowered metabolism. While the reason for the reduction in metabolic rate is unknown, hyperphagia results from the lack of melanocyte stimulating hormone (MSH) secretion (Cheung et al., *Endocrinology* 138:4489-92 (1997); Thiele et al., *Am. J Physiol* 274:248-54 (1998)). No involvement of ataxin-2 is known in any of these mechanisms. On the other hand, purely behavioral alterations could also account for the phenotype, although reduced physical activity was not observed. The rapid response to a low-calorie diet suggests that these mice could be hyperphagic.

It is understood that modifications which do not substantially affect the activity of the various embodiments of this invention are also provided within the definition of the invention provided herein. Accordingly, the following examples are intended to illustrate but not limit the present invention.

EXAMPLE I

Targeted Disruption of the Mouse SCA2 Gene

The mouse homolog of the SCA2 gene was previously identified and characterized (Nechiporuk et al., 1998). The mouse SCA2 cDNA was isolated from a 129SV genomic library (Stratagene, La Jolla, Calif.), containing a 12.2 kb fragment that included exon 1 of the murine SCA2 gene. Presence of exon 1 in this fragment was confirmed by restriction enzyme mapping and southern analysis. A targeting construct was then generated in pBlueScript, in which a PGK-Neomycin resistance cassette was inserted into a NotI site in exon 1 as illustrated in FIG. 1A. This construct was linearized and electroporated into 129/SvJ embryonic stem (ES) cells (Genome Systems, St. Louis, Mo., now Incyte Genomics). Cells were grown under double selection in G418 and gancyclovir (GibcoBRL, Rockville, Md.) as described (Köntgen and Stewart, *Meth Enzymol.* 225:878-889 (1993)).

FIG. 1 depicts the SCA2 gene and targeting strategy. Replacement of 1.6 kb of the SCA2 gene with the Neo cassette by homologous recombination resulting in disruption of exon 1. Restriction sites: B=BamHI, E=EcoRI, N=Not I, P=Pst I, X=Xho I. (B) Identification of the targeted allele by southern hybridization. The targeted allele is diagnosed by a 7 kb increase in an XhoI restriction fragment when probed with the indicated 5' external fragment and a 6.5 kb decrease when probed with a BamH I fragment hybridizing with the 3' end. (C) Overview of the ataxin-2 protein sequence including known motifs. The polyglutamine tract is not present in the mouse. An acidic domain contains motifs highly similar to the Sm proteins. Ataxin-2 binds A2BP1 via its C-terminus. A putative binding site to the C-terminus of Poly(A)-binding protein (PABC) is located at aa 908-925.

Targeted ES cell clones were screened by Southern Blot (FIG. 1B). Almost 25% of ES cell clones carried the correct mutation. Positive clones were injected into C57Bl/6 blastocysts to generate chimeras and implanted into pseudopregnant females. Germline transmission was achieved by crossing chimeric males with C57Bl/6 females. To confirm the loss of SCA2 gene expression in nullizygous animals, RNA was prepared from various tissues of wild type and SCA2 (−/−) mice.

Figure 2:
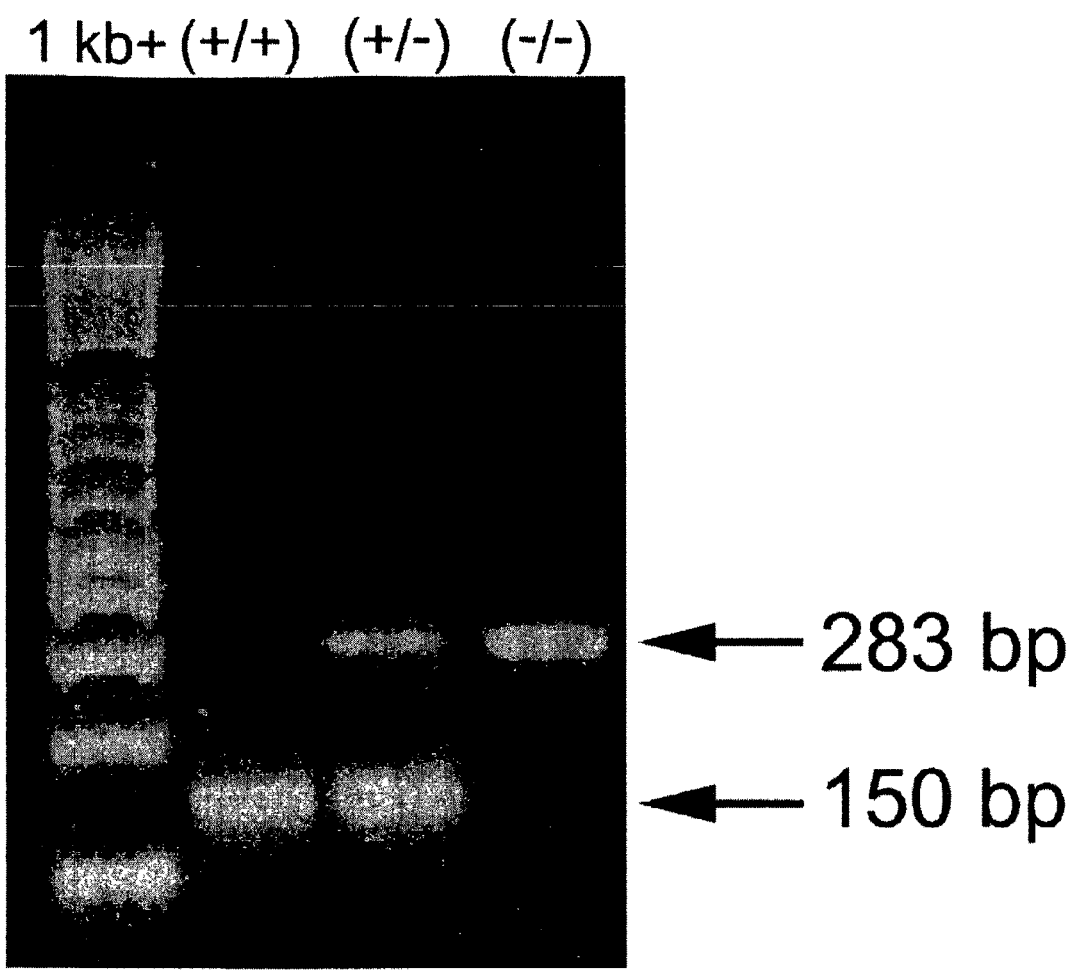
FIG. 2 shows results of PCR analysis to detect an inserted neomycin cassette in a SCA2 mutant mouse (283 bp product) compared to a wild type mouse (150 bp product).

Northern analysis using a probe to the 3' end of the mouse SCA2 gene and RT-PCR revealed the absence of full-length mRNA (FIG. 2). For northern analysis, total RNA samples were extracted from different regions of mouse brain and skeletal muscle using the RNeasy kit (Qiagen, Valencia, Calif.). RNA was elecrophoresed through 1.2% agarose gel and blotted onto GeneScreen Plus membrane (NEN Life Science, Boston, Mass.). A probe was labeled with α-($^{32}$P)dCTP by RadPrime random priming kit (GibcoBRL). The conditions of hybridization and washing followed the supplier's protocols (NEN). The relative loading and integrity of total RNA on each lane were confirmed by subsequent hybridization with β-actin (Clontech, Palo Alto, Calif.).

Reverse-transcription PCR performed from cerebral cortex total RNA showed absence of product in the targeted locus. The control (A2BP1) was unaffected. RT-PCR was performed on cerebral cortex and skeletal muscle tissue with the Reverse Transcription System (Promega, Madison, Wis.) set according to the supplier's protocol. The primer pair used for detection of the SCA2 gene transcript was identical to the one used for genotyping (mSCA2M20A and B), which is described below. Primers for the control (A2BP1) were mA2bp1-C (5' GACCCGAGAAACCACCAGT') (SEQ ID NO:7) and mA2bp1-D (5' AGAGGCAACGAATTAG-GATGT') (SEQ ID NO:8).

Western blot analysis using specific antibodies to ataxin-2 confirmed absence of the 120 kD ataxin-2 protein in mice homozygous for the SCA2 gene disruption. Absence of the protein was also confirmed by immunocytochemistry assay of various tissues. Fresh tissue was obtained from two month old SCA2 (−/−) and wild-type control mice. After homogenization, the lysate was resuspended in triple detergent buffer (100 mM Tris-HCl, pH 7.4, 1 mM EGTA, 1% NP40, 0.5% SDS, 0.5% deoxycholic acid, 1 mM Pefabloc Sc, 1 µg/ml Pepstatin A, 2 µg/ml Aprotinin, 50 µg/ml Leupeptin, all from Roche, Indianapolis, IN) and homogenized using a polytron homogenizer. The protein extracts were first centrifuged at 1000g (3100 rpm in a JA 17 rotor) for 5 min. The supenatant was recentrifuged at 105,000g (54,000 rpm in a TLN100 rotor) for 1 hr. It was then aliquoted and stored at -80° C. Protein concentration was determined using the Bradford Protein Assay Kit (BioRad, Hercules, Calif.). Prior to loading onto polyacrylamide gels, proteins were concentrated using a Microcon 10 (Amicon, Bedford, Mass) or acetone precipitation. 100 µg of protein was loaded per lane in a precast 4-20% gradient SDS-polyacrylamide mini-gel (BioRad) and electrophoresed at 100 V for 1-2 hrs. Proteins were transferred to nitrocellulose filter (Amersham, Piscataway, N.J.). The filter was rinsed briefly with TBS (150 mM NaCl, 50 mM Tris-HCl, pH 8.0), and blocked for 1 hr with 5% nonfat dry milk (BioRad) for rabbit custom-made primary antibodies. The filter was then incubated with the desired dilution of tested antibodies for 1 h at room temperature. The primary antibody was detected with the ECL western blotting detection system (Amersham) using anti-rabbit IgG antibodies conjugated with horseradish peroxidase.

Figure 3:
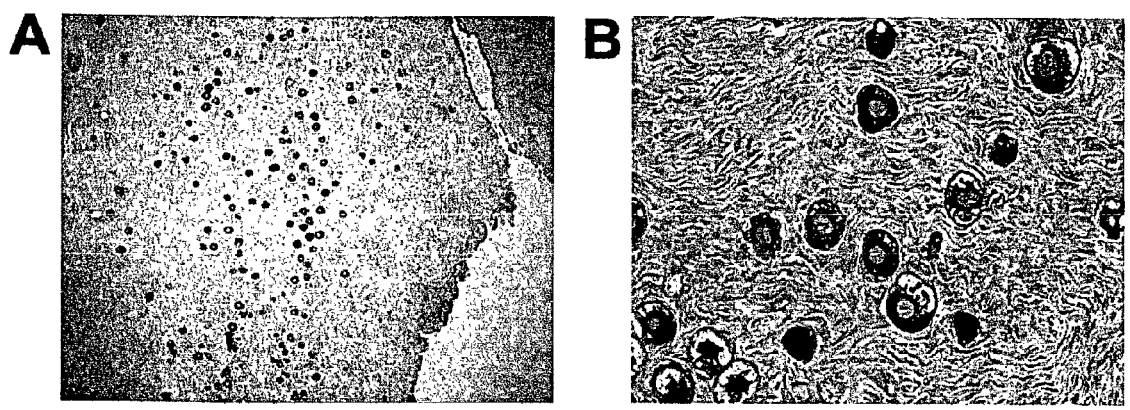
FIG. 3 shows ataxin-2 expression in oocytes in primary follicles of human ovary sections.

Specific expression of ataxin-2 was also shown in primary follicles of human ovary sections. FIG. 3A shows immunocytochemistry using SCA2-B antibody, which indicates highly specific staining of oocytes in primary follicles and little background staining in the ovarian stroma. FIG. 3B shows a 20×magnification, which indicates that immunoreactivity is confined to the cytoplasm of the oocyte and the surrounding zona pellucida whereas the nucleus is spared.

Two rabbit anti-ataxin-2 antisera used for Western analysis were raised as described previously (Huynh et al., *Ann. Neurol.*, 45:232-241 (1999); Huynh et al., *Nat. Genet.*, 26:44-50 (2000)). Mouse monoclonal antibodies to y-adaptin and transGolgi58 were purchased from Sigma (St. Louis, Mo.). Adult mouse tissue was obtained from wild-type and homozygous SCA2 knockout animals. Embryonic sections were purchased from Novagen (Madison, Wis.). Six-micron sections were cut and mounted onto Superplus microscopic slides (Fisher Scientific, Pittsburgh, Pa.). Human paraffin-embedded ovarian sections were obtained from a surgical specimen. The sections were rehydrated by rinsing twice at 5 minute intervals in xylene, 100% ethanol, 95% ethanol, and 70% ethanol. After deparaffinization, sections were treated with a protease cocktail, blocked with avidin/biotin and 3% normal goat serum. Sections were then incubated with 10-20 mg/ml of affinity purified ataxin-2 antibody overnight at 4° C. Primary antibody was detected using the Vector rabbit ABC elite Peroxidase kit (Vector, Burlingame, Calif.), enhanced by DAB enhancer, and visualized with diaminobenzidine (DAB, Biomeda, Hayward, Calif). Sections were counterstained with aqueous hematoxylin (Zymed, S. San Francisco, Calif.). Controls consisted of antibody preabsorbed with 100 mM of the respective peptide and pre-immune sera at comparable concentrations (1/500). All slides for direct comparison were processed in a single batch to minimize variability.

Genotyping PCR amplified a 283 bp product from the inserted Neomycin cassette in the mutant and a 150 bp product in the wild type (exon 1). Genotyping was performed by PCR with two sets of primers 5'-CCAGAGGGAGGCACAG-TAGT-3' (Primer mSCA2M20A) (SEQ ID NO:9) and 5'-TTAAAACGGAGAGGCAGATG-3' (SEQ ID NO:10) (Primer mSCA2M20B) that amplify exon 1 of the murine SCA2 gene. The second set, 5'-GCTTGGGTGGA GAGGC-TATTC-3' (SEQ ID NO:11)(Primer Neo-A) and 5'-CAAG-GTGAGATGACAGGAGATC-3' (SEQ ID NO:12)(Primer Neo-B) amplifies the inserted Neomycin resistance cassette. At PCR conditions of 95° C./5' denaturation, 35 cycles of 94° C./1' denaturation, 55° C./30" annealing and 72° C./30" extension, a 150 bp amplicon will be generated from SCA2-exon 1 and a 283 bp amplicon from the Neo cassette. FIG. 2 shows the 283 bp product from the inserted Neomycin cassette in the mutant and a 150 bp product in the wild type (exon 1).

The chromosomal localization of the mouse SCA2 gene was determined by PCR amplification of a mouse T31 radiation hybrid panel (McCarthy et al., *Genome Res.* 7:1153-1161 (1997)) with exon 1-specific primers. The gene was mapped to mouse chromosome 5 at 13.01 cR from the marker D5Mit368 (lod>3.0) in a large region syntenic with human chromosome 12. The Mouse/Hamster Radiation Hybrid Panel (Research Genetics, Huntsville, Ala.) was also used to map the chromosomal localization of the mouse SCA2 gene. Primers were the same exon 1-specific primers that were used for genotyping (mSCA2M20A and mSCA2M20B). Likewise, PCR conditions were the same. PCR products were analyzed on a 2% agarose gel by ethidium bromide staining and confirmed by subsequent southern blot analysis using an A2BP1 cDNA containing the 5' UTR as a probe. The result was analyzed using the server at genome.wi.mit.edu/cgi-bin/contig/rhmapper.pl. The same primer pair was also used to screen the monochromosomal Somatic Cell Hybrid Panel (Bios, New Haven, Conn.) to confirm the mapping result.

Phenotypic analysis was performed on the original C57Bl/6-129 mixed strain, which was subsequently backcrossed into a pure C57BL/6 background.

The combined results of these studies demonstrate that no ataxin-2 is produced in homozygous SCA2 knockout mice. Loss of ataxin-2 did not affect the expression of ataxin-2 binding protein 1 (A2BP1), indicating that mouse A2BP1 expression is not influenced by the level of ataxin-2.

EXAMPLE II

Characterization of SCA2 Knock-Out Mice

This example shows that the phenotype of a SCA2 knock-out mouse includes obesity and memory impairment.

Expression of SCA2 was examined in developing mouse embryos. As previously described, the SCA2 mRNA can be detected from day 8 of gestation (Nechiporuk et al., *Hum.*

*Mol. Genet.*, 7:1301-1309 (1998)). Ataxin-2 antibodies were used to examine its expression in paraffin-embedded sections of the mouse embryo at different stages. Ataxin-2 immunoreactivity was detected in heart and mesenchymal tissues throughout all embryonic stages. In contrast, it was absent in the primitive nervous system until day 12. Overall, the labeling was substantially identical a related mouse gene, A2bp1.

Homozygous SCA2$^{-/-}$ mice were viable, fertile and showed no obvious defects and no increase in morbidity when compared to their wild-type littermates. No abnormal behavioral patterns were observed in open-cage observation. Wild type and homozygous SCA2$^{-/-}$ mice performed equally well in motor performance tests such as the accelerating rota-rod. Careful histopathological examination of the central nervous system, heart, skeletal muscle, liver and kidney demonstrated no observable differences between KO animals and their WT littermates.

However, as SCA2$^{-/-}$ mice aged, a SCA2 knockout phenotype became observable. Specifically, when maintained on a regular NIH rodent diet, homozygous SCA2 knockouts showed marked adult-onset obesity. While the body weight at birth and at weaning age is identical to wild type mice, there is a progressive increase at 3 months (10% higher than WT), 6 months (29.8%) and 1 year of age (66%). The animals did not appear to be hypoactive, and the increased body weight was rapidly responsive to a low-calorie diet. Present in male and female mice, this phenotype was associated with breeding problems.

Figure 4:
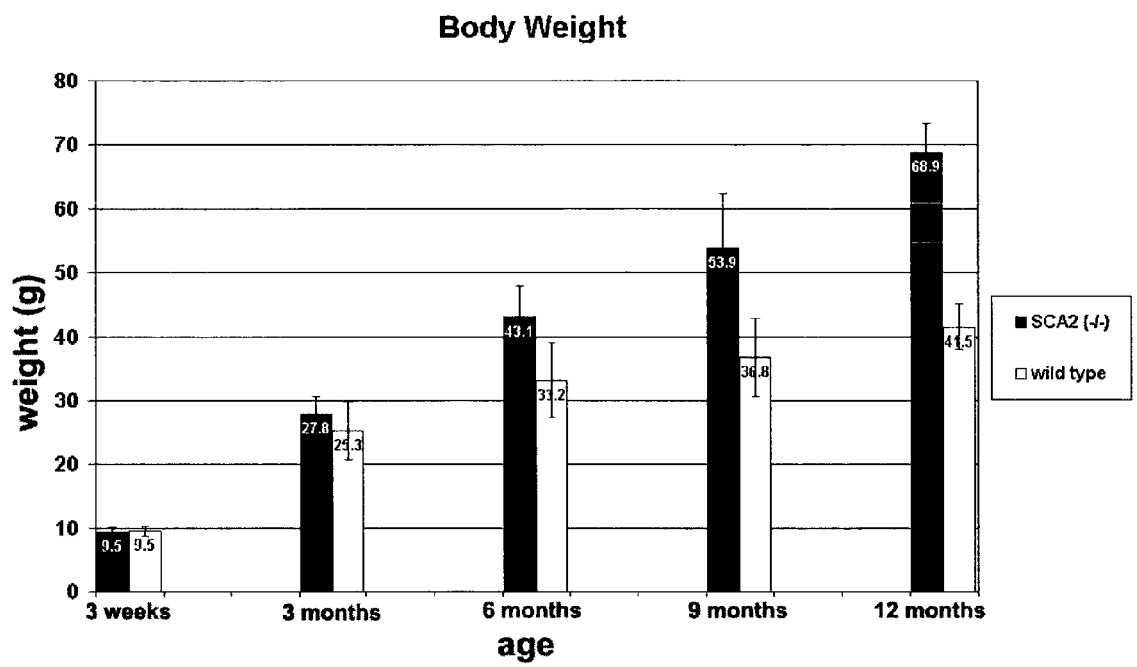
FIG. 4 shows growth curves that indicate the weekly weights of wild type and SCA2 mutant mice at weaning, then at 3, 6, 9 and 12 months.

FIG. 4 shows growth curves that indicate the weekly weights at weaning, then at 3, 6, 9 and 12 months. While there is no significant difference at weaning age, the difference between KO and WT animals widens with age In addition, the SCA2 knockouts exhibited memory impairment. The absence of ataxin-2 expression led to CNS memory deficits. In particular, the SCA2 knockouts were found to perform poorly in a hippocampal memory test.

In summary, this example shows that the phenotype of a SCA2 knockout mouse includes obesity, which can include late onset obesity, and memory impairment.

EXAMPLE III

Identification of Potential Ataxia-2

Therapeutic Target Genes

This example describes the identification of several genes having altered expression in SCA2 knockout mice in comparison to wild type mice. The identified genes represent potential ataxia-2 therapeutic targets for treating obesity, memory impairment and related disorders.

Gene expression in SCA2 knockout mice and wild type mice was compared in several tissues, including cerebrum, cerebellum, heart and skeletal muscle. Gene expression analysis was performed using the Affymetrix chip containing 12,000 mouse genes according to the substantially according to the manufacturer's instructions.

Several genes were expressed at significantly different levels in SCA2 knockout compared to wild type mice. As shown in Table 1, both increases and decreases in gene expression levels were observed, and in some cases these changes in gene expression level were tissue-specific.

TABLE 1

Genes Having Altered Expression in SCA2 Knockout Mice as Compared to Wild Type Mice

| Gene name | Tissues | Increase or Decreased? |
|---|---|---|
| Peroxiredoxin-2 | cerebrum, cerebellum and skeletal muscle | decreased |
| 3-oxoacid CoA transferase | cerebrum, cerebellum, heart and skeletal muscle | decreased |
| stearoyl-CoA desaturase I | cerebrum, cerebellum and heart | decreased |
| nuclear factor 1-X | cerebrum and heart | decreased |
| EST AA002843 | cerebrum, cerebellum and heart | decreased |
| inactive X-specific transcript | cerebellum and skeletal muscle | increased |
| erythroid differentiation regulator | cerebrum and heart | increased |
| nuclear ribonucleoprotein L | cerebrum, heart and skeletal muscle | increased |
| EST AW258842 | cerebrum, cerebellum and heart | increased |

The functions of many of these genes have been described. For example, the peroxiredoxin-2 gene has a role in reducing oxidative stress, the inactive X-specific transcript (XIST) gene has a role in X-inactivation, and the erythroid differentiation regulator gene has a ubiquitous role in regulating differentiation. The functions of uncharacterized genes, such as those contained in ESTs can be determined based on structural homologies with other genes, as well as using other well known methods for determining gene function.

This example shows that the expression of several genes is modulated in mice homozygous for a deletion of the SCA2 gene in comparison to wild type mice.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A mutant knockout mouse whose genome comprises a disruption of an endogenous SCA2 gene, wherein said SCA2 gene is disrupted and wherein ataxin-2 protein is not expressed from said disrupted SCA2 gene, and wherein said mutant knockout mouse exhibits an obesity phenotype.

2. The mutant knockout mouse of claim 1, wherein said mouse is a homozygous SCA2 mutant mouse.

3. The mutant knockout mouse of claim 1, wherein said mouse is a heterozygous SCA2 mutant mouse.

4. The mutant knockout mouse of claim 1, wherein said SCA2 gene is disrupted by homologous recombination using a DNA construct comprising exon 1 of said SCA2 gene.

5. The mutant knockout mouse of claim 4, wherein a selectable marker is inserted into exon 1 of said SCA2 gene.

6. The mutant knockout mouse of claim 5, wherein said selectable marker comprises a neomycin resistance gene.

7. The mutant knockout mouse of claim 2, wherein said mutant knockout mouse further exhibits a phenotype selected from:
   (a) impaired memory;
   (b) decreased expression of a nucleic acid encoding peroxiredoxin-2, 3-oxoacid CoA transferase, stearoyl-CoA desaturase I, nuclear factor 1-X or EST AA002843; and
   (c) increased expression of a nucleic acid encoding inactive X-specific transcript, erythroid differentiation regulator, nuclear ribonucleoprotein L or EST AW258842.

8. The mutant knockout mouse of claim 7, wherein said phenotype is impaired memory.

9. The mutant knockout mouse of claim 7, wherein said nucleic acid having decreased expression encodes peroxiredoxin-2.

10. The mutant knockout mouse of claim 7, wherein said nucleic acid having decreased expression encodes 3-oxoacid CoA transferase.

11. The mutant knockout mouse of claim 7, wherein said nucleic acid having decreased expression encodes stearoyl-CoA desaturase I.

12. The mutant knockout mouse of claim 7, wherein said nucleic acid having decreased expression encodes nuclear factor 1-X.

13. The mutant knockout mouse of claim 7, wherein said nucleic acid having decreased expression encodes EST AA002843.

14. The mutant knockout mouse of claim 7, wherein said nucleic acid having increased expression encodes inactive X-specific transcript.

15. The mutant knockout mouse of claim 7, wherein said nucleic acid having increased expression encodes erythroid differentiation regulator.

16. The mutant knockout mouse of claim 7, wherein said nucleic acid having increased expression encodes nuclear ribonucleoprotein L.

17. The mutant knockout mouse of claim 7, wherein said nucleic acid having increased expression encodes EST AW258842.

* * * * *

SEQUENCE LISTING

<160> NUMBER OF SEQ ID NOS: 12

<210> SEQ ID NO 1
<211> LENGTH: 1257
<212> TYPE: DNA
<213> ORGANISM: Mus musculus
<220> FEATURE:
<221> NAME/KEY: CDS

<222> LOCATION: (2)...(1255)

<400> SEQUENCE: 1

```
  g cac gag ggg ccg ctc acc atg tcg ctg aag ccg cag ccg cag ccg ccc        49
    His Glu Gly Pro Leu Thr Met Ser Leu Lys Pro Gln Pro Gln Pro Pro
     1               5                  10                  15 gcg ccc gcc act ggc cgc aag ccc ggc ggc ggc ctg ctc tcg tcg ccc            97
Ala Pro Ala Thr Gly Arg Lys Pro Gly Gly Gly Leu Leu Ser Ser Pro
             20                  25                  30 ggc gcc gcg ccg gcc tcg gcc gcg gtg acc tcg gct tcc gtg gtg ccg           145
Gly Ala Ala Pro Ala Ser Ala Ala Val Thr Ser Ala Ser Val Val Pro
         35                  40                  45 gcc ccg gcc gcg ccg gtg gcg tct tcc tcg gcg gcc gcg ggc ggc ggg           193
Ala Pro Ala Ala Pro Val Ala Ser Ser Ser Ala Ala Ala Gly Gly Gly
     50                  55                  60 cgt ccc ggc ctg ggc aga ggt cgg aac agt agc aaa gga ctg cct cag           241
Arg Pro Gly Leu Gly Arg Gly Arg Asn Ser Ser Lys Gly Leu Pro Gln
 65                  70                  75                  80 cct acg att tct ttt gat gga atc tat gca aac gtg agg atg gtt cat           289
Pro Thr Ile Ser Phe Asp Gly Ile Tyr Ala Asn Val Arg Met Val His
                 85                  90                  95 ata ctt acg tca gtt gtt gga tcg aaa tgt gaa gta caa gtg aaa aac           337
Ile Leu Thr Ser Val Val Gly Ser Lys Cys Glu Val Gln Val Lys Asn
            100                 105                 110 gga ggc ata tat gaa gga gtt ttt aaa aca tac agt cct aag tgt gac           385
Gly Gly Ile Tyr Glu Gly Val Phe Lys Thr Tyr Ser Pro Lys Cys Asp
        115                 120                 125 ttg gta ctt gat gct gca cat gag aaa agt aca gaa tcc agt tcg ggg           433
Leu Val Leu Asp Ala Ala His Glu Lys Ser Thr Glu Ser Ser Ser Gly
    130                 135                 140 cca aaa cgt gaa gaa ata atg gag agt gtt ttg ttc aaa tgc tca gac           481
Pro Lys Arg Glu Glu Ile Met Glu Ser Val Leu Phe Lys Cys Ser Asp
145                 150                 155                 160 ttc gtt gtg gta cag ttt aaa gat aca gac tcc agt tat gca cgg aga           529
Phe Val Val Val Gln Phe Lys Asp Thr Asp Ser Ser Tyr Ala Arg Arg
                165                 170                 175 gat gct ttt act gac tct gct ctc agc gca aag gtg aat ggt gag cac           577
Asp Ala Phe Thr Asp Ser Ala Leu Ser Ala Lys Val Asn Gly Glu His
            180                 185                 190 aag gag aag gac ctg gag ccc tgg gat gca ggg gag ctc acg gcc agc           625
Lys Glu Lys Asp Leu Glu Pro Trp Asp Ala Gly Glu Leu Thr Ala Ser
        195                 200                 205 gag gag ctg gag ctg gag aat gat gtg tct aat gga tgg gac ccc aat           673
Glu Glu Leu Glu Leu Glu Asn Asp Val Ser Asn Gly Trp Asp Pro Asn
    210                 215                 220 gac atg ttt cga tat aat gaa gag aat tat ggt gtg gtg tcc aca tat           721
Asp Met Phe Arg Tyr Asn Glu Glu Asn Tyr Gly Val Val Ser Thr Tyr
225                 230                 235                 240 gat agc agt tta tct tca tat acg gtt cct tta gaa agg gac aac tca           769
Asp Ser Ser Leu Ser Ser Tyr Thr Val Pro Leu Glu Arg Asp Asn Ser
                245                 250                 255 gaa gaa ttt ctt aaa cgg gag gca agg gca aac cag tta gca gaa gaa           817
Glu Glu Phe Leu Lys Arg Glu Ala Arg Ala Asn Gln Leu Ala Glu Glu
            260                 265                 270 att gaa tcc agt gct cag tac aaa gct cgt gtc gcc ctt gag aat gat           865
Ile Glu Ser Ser Ala Gln Tyr Lys Ala Arg Val Ala Leu Glu Asn Asp
        275                 280                 285 gac cgg agt gag gaa gaa aaa tac aca gca gtc cag aga aac tgc agt           913
Asp Arg Ser Glu Glu Glu Lys Tyr Thr Ala Val Gln Arg Asn Cys Ser
    290                 295                 300
```

```
gac cgg gag ggg cat ggc ccc aac act agg gac aat aaa tat att cct    961
Asp Arg Glu Gly His Gly Pro Asn Thr Arg Asp Asn Lys Tyr Ile Pro
305                 310                 315                 320 cct gga caa aga aac aga gaa gtc cta tcc tgg gga agt ggg aga cag   1009
Pro Gly Gln Arg Asn Arg Glu Val Leu Ser Trp Gly Ser Gly Arg Gln
                325                 330                 335 agc tca cca cgg atg ggc cag cct ggg cca ggc tcc atg ccg tca aga   1057
Ser Ser Pro Arg Met Gly Gln Pro Gly Pro Gly Ser Met Pro Ser Arg
            340                 345                 350 gct gct tct cac act tca gat ttc aac ccg aac gct ggc tca gac caa   1105
Ala Ala Ser His Thr Ser Asp Phe Asn Pro Asn Ala Gly Ser Asp Gln
        355                 360                 365 aga gta gtt aat gga ggt gtt ccc tgg cca tcg cct tgc cca tct cct   1153
Arg Val Val Asn Gly Gly Val Pro Trp Pro Ser Pro Cys Pro Ser Pro
370                 375                 380 tcc tct cgc cca cct tct cgc tac cag tca ggt ccc aac tct ctt cca   1201
Ser Ser Arg Pro Pro Ser Arg Tyr Gln Ser Gly Pro Asn Ser Leu Pro
385                 390                 395                 400 cct cgg gca gcc acc cct aca cgg cct cgt gcc gaa ttc ctg cag ccc   1249
Pro Arg Ala Ala Thr Pro Thr Arg Pro Arg Ala Glu Phe Leu Gln Pro
                405                 410                 415 ggg gat cc                                                        1257
Gly Asp
```

<210> SEQ ID NO 2
<211> LENGTH: 418
<212> TYPE: PRT
<213> ORGANISM: Mus musculus

<400> SEQUENCE: 2

```
His Glu Gly Pro Leu Thr Met Ser Leu Lys Pro Gln Pro Gln Pro Pro
1               5                   10                  15

Ala Pro Ala Thr Gly Arg Lys Pro Gly Gly Leu Leu Ser Ser Pro
            20                  25                  30

Gly Ala Ala Pro Ala Ser Ala Ala Val Thr Ser Ala Ser Val Val Pro
        35                  40                  45

Ala Pro Ala Ala Pro Val Ala Ser Ser Ala Ala Ala Gly Gly Gly
    50                  55                  60

Arg Pro Gly Leu Gly Arg Gly Arg Asn Ser Ser Lys Gly Leu Pro Gln
65                  70                  75                  80

Pro Thr Ile Ser Phe Asp Gly Ile Tyr Ala Asn Val Arg Met Val His
                85                  90                  95

Ile Leu Thr Ser Val Val Gly Ser Lys Cys Glu Val Gln Val Lys Asn
            100                 105                 110

Gly Gly Ile Tyr Glu Gly Val Phe Lys Thr Tyr Ser Pro Lys Cys Asp
        115                 120                 125

Leu Val Leu Asp Ala Ala His Glu Lys Ser Thr Glu Ser Ser Ser Gly
    130                 135                 140

Pro Lys Arg Glu Glu Ile Met Glu Ser Val Leu Phe Lys Cys Ser Asp
145                 150                 155                 160

Phe Val Val Gln Phe Lys Asp Thr Asp Ser Ser Tyr Ala Arg Arg
                165                 170                 175

Asp Ala Phe Thr Asp Ser Ala Leu Ser Ala Lys Val Asn Gly Glu His
            180                 185                 190

Lys Glu Lys Asp Leu Glu Pro Trp Asp Ala Gly Glu Leu Thr Ala Ser
        195                 200                 205
```

```
Glu Glu Leu Glu Leu Glu Asn Asp Val Ser Asn Gly Trp Asp Pro Asn
    210                 215                 220
Asp Met Phe Arg Tyr Asn Glu Glu Asn Tyr Gly Val Val Ser Thr Tyr
225                 230                 235                 240
Asp Ser Ser Leu Ser Ser Tyr Thr Val Pro Leu Glu Arg Asp Asn Ser
            245                 250                 255
Glu Glu Phe Leu Lys Arg Glu Ala Arg Ala Asn Gln Leu Ala Glu Glu
        260                 265                 270
Ile Glu Ser Ser Ala Gln Tyr Lys Ala Arg Val Ala Leu Glu Asn Asp
    275                 280                 285
Asp Arg Ser Glu Glu Lys Tyr Thr Ala Val Gln Arg Asn Cys Ser
290                 295                 300
Asp Arg Glu Gly His Gly Pro Asn Thr Arg Asp Asn Lys Tyr Ile Pro
305                 310                 315                 320
Pro Gly Gln Arg Asn Arg Glu Val Leu Ser Trp Gly Ser Gly Arg Gln
            325                 330                 335
Ser Ser Pro Arg Met Gly Gln Pro Gly Pro Gly Ser Met Pro Ser Arg
        340                 345                 350
Ala Ala Ser His Thr Ser Asp Phe Asn Pro Asn Ala Gly Ser Asp Gln
    355                 360                 365
Arg Val Val Asn Gly Val Pro Trp Pro Ser Pro Cys Pro Ser Pro
370                 375                 380
Ser Ser Arg Pro Pro Ser Arg Tyr Gln Ser Gly Pro Asn Ser Leu Pro
385                 390                 395                 400
Pro Arg Ala Ala Thr Pro Thr Arg Pro Arg Ala Glu Phe Leu Gln Pro
            405                 410                 415
Gly Asp

<210> SEQ ID NO 3
<211> LENGTH: 4225
<212> TYPE: DNA
<213> ORGANISM: Mus musculus
<220> FEATURE:
<221> NAME/KEY: CDS
<222> LOCATION: (27)...(3884)
<220> FEATURE:
<221> NAME/KEY: misc_feature
<222> LOCATION: (222)...(224)
<223> OTHER INFORMATION: ccs=Pro

<400> SEQUENCE: 3
ccgtccggtc cgccagcccg ggtccc atg cgt tcg tcc acc gcc gcc gtt cag      53
                              Met Arg Ser Ser Thr Ala Ala Val Gln
                                1               5 cgg ccc gcg gcg ggg gac ccc gag ccg cgc cgc ccg gcg ggc tgg gcc     101
Arg Pro Ala Ala Gly Asp Pro Glu Pro Arg Arg Pro Ala Gly Trp Ala
 10                  15                  20                  25 gcg cgg cgc tcg ctc ccg cgg acg gcg cgg cgc ggg cgg ggc ggc         149
Ala Arg Arg Ser Leu Pro Arg Thr Ala Arg Arg Gly Arg Gly Gly
                 30                  35                  40 gcg gtg gcg tat ccc tcc gcc ggc cct ccc cgc ggc ccc ggc gcc         197
Ala Val Ala Tyr Pro Ser Ala Gly Pro Pro Arg Gly Pro Gly Ala
             45                  50                  55 cct ccc cgc ggg ccg cgc tcg cca ccs tgc gcc tca gac tgt ttt ggt     245
Pro Pro Arg Gly Pro Arg Ser Pro Xaa Cys Ala Ser Asp Cys Phe Gly
             60                  65                  70 agc aac ggc cac ggc gcg tcc cgg ccc ggc tcc cgg cgg ctg ctc ggt     293
Ser Asn Gly His Gly Ala Ser Arg Pro Gly Ser Arg Arg Leu Leu Gly
 75                  80                  85
```

| | | |
|---|---|---|
| gtc tgc ggg cct ccc cgc ccc ttc gtc gtt gtc ctg ctc gct ctg gcc<br>Val Cys Gly Pro Pro Arg Pro Phe Val Val Val Leu Leu Ala Leu Ala<br>90                           95                     100                   105 | 341 |
| ccg gcg gcc acg ccg gcc cgc gcc tgc ccc ggc gtc cgc gcg tcc<br>Pro Ala Ala Thr Pro Ala Arg Ala Cys Pro Pro Gly Val Arg Ala Ser<br>               110                     115                    120 | 389 |
| ccg ccg cgc tcc ggc gtc tcc tcc tcg gcg cgc ccg gca ccc ggc tgt<br>Pro Pro Arg Ser Gly Val Ser Ser Ser Ala Arg Pro Ala Pro Gly Cys<br>        125                     130                    135 | 437 |
| ccc cgc ccg gcg tgc gag ccg gtg tat ggg ccg ctc acc atg tcg ctg<br>Pro Arg Pro Ala Cys Glu Pro Val Tyr Gly Pro Leu Thr Met Ser Leu<br>      140                    145                    150 | 485 |
| aag ccg cag ccg cag ccg ccc gcg ccc gcc act ggc cgc aag ccc ggc<br>Lys Pro Gln Pro Gln Pro Pro Ala Pro Ala Thr Gly Arg Lys Pro Gly<br>155                     160                    165 | 533 |
| ggc ggc ctg ctc tcg tcg ccc ggc gcc gcg ccg gcc tcg gcc gcg gtg<br>Gly Gly Leu Leu Ser Ser Pro Gly Ala Ala Pro Ala Ser Ala Ala Val<br>170                  175                    180                    185 | 581 |
| acc tcg gct tcc gtg gtg ccg gcc ccg gcc gcg ccg gtg gcg tct tcc<br>Thr Ser Ala Ser Val Val Pro Ala Pro Ala Ala Pro Val Ala Ser Ser<br>                 190                    195                    200 | 629 |
| tcg gcg gcc gcg ggc ggc ggg cgt ccc ggc ctg ggc aga ggt cgg aac<br>Ser Ala Ala Ala Gly Gly Gly Arg Pro Gly Leu Gly Arg Gly Arg Asn<br>            205                     210                    215 | 677 |
| agt agc aaa gga ctg cct cag cct acg att tct ttt gat gga atc tat<br>Ser Ser Lys Gly Leu Pro Gln Pro Thr Ile Ser Phe Asp Gly Ile Tyr<br>           220                     225                    230 | 725 |
| gca aac gtg agg atg gtt cat ata ctt acg tca gtt gtt gga tcg aaa<br>Ala Asn Val Arg Met Val His Ile Leu Thr Ser Val Val Gly Ser Lys<br>235                     240                    245 | 773 |
| tgt gaa gta caa gtg aaa aac gga ggc ata tat gaa gga gtt ttt aaa<br>Cys Glu Val Gln Val Lys Asn Gly Gly Ile Tyr Glu Gly Val Phe Lys<br>250                     255                    260                    265 | 821 |
| aca tac agt cct aag tgt gac ttg gta ctt gat gct gca cat gag aaa<br>Thr Tyr Ser Pro Lys Cys Asp Leu Val Leu Asp Ala Ala His Glu Lys<br>                 270                    275                    280 | 869 |
| agt aca gaa tcc agt tcg ggg cca aaa cgt gaa gaa ata atg gag agt<br>Ser Thr Glu Ser Ser Ser Gly Pro Lys Arg Glu Glu Ile Met Glu Ser<br>            285                     290                    295 | 917 |
| gtt ttg ttc aaa tgc tca gac ttc gtt gtg gta cag ttt aaa gat aca<br>Val Leu Phe Lys Cys Ser Asp Phe Val Val Val Gln Phe Lys Asp Thr<br>           300                     305                    310 | 965 |
| gac tcc agt tat gca cgg aga gat gct ttt act gac tct gct ctc agc<br>Asp Ser Ser Tyr Ala Arg Arg Asp Ala Phe Thr Asp Ser Ala Leu Ser<br>315                     320                    325 | 1013 |
| gca aag gtg aat ggt gag cac aag gag aag gac ctg gag ccc tgg gat<br>Ala Lys Val Asn Gly Glu His Lys Glu Lys Asp Leu Glu Pro Trp Asp<br>330                     335                    340                    345 | 1061 |
| gca ggg gag ctc acg gcc agc gag gag ctg gag ctg gag aat gat gtg<br>Ala Gly Glu Leu Thr Ala Ser Glu Glu Leu Glu Leu Glu Asn Asp Val<br>                 350                    355                    360 | 1109 |
| tct aat gga tgg gac ccc aat gac atg ttt cga tat aat gaa gag aat<br>Ser Asn Gly Trp Asp Pro Asn Asp Met Phe Arg Tyr Asn Glu Glu Asn<br>           365                     370                    375 | 1157 |
| tat ggt gtg gtg tcc aca tat gat agc agt tta tct tca tat acg gtt<br>Tyr Gly Val Val Ser Thr Tyr Asp Ser Ser Leu Ser Ser Tyr Thr Val<br>           380                     385                    390 | 1205 |
| cct tta gaa agg gac aac tca gaa gaa ttt ctt aaa cgg gag gca agg<br>Pro Leu Glu Arg Asp Asn Ser Glu Glu Phe Leu Lys Arg Glu Ala Arg | 1253 |

-continued

```
                395                 400                 405
gca aac cag tta gca gaa gaa att gaa tcc agt gct cag tac aaa gct    1301
Ala Asn Gln Leu Ala Glu Glu Ile Glu Ser Ser Ala Gln Tyr Lys Ala
410                 415                 420                 425 cgt gtc gcc ctt gag aat gat gac cgg agt gag gaa gaa aaa tac aca    1349
Arg Val Ala Leu Glu Asn Asp Asp Arg Ser Glu Glu Glu Lys Tyr Thr
                430                 435                 440 gca gtc cag aga aac tgc agt gac cgg gag ggg cat ggc ccc aac act    1397
Ala Val Gln Arg Asn Cys Ser Asp Arg Glu Gly His Gly Pro Asn Thr
            445                 450                 455 agg gac aat aaa tat att cct cct gga caa aga aac aga gaa gtc cta    1445
Arg Asp Asn Lys Tyr Ile Pro Pro Gly Gln Arg Asn Arg Glu Val Leu
        460                 465                 470 tcc tgg gga agt ggg aga cag agc tca cca cgg atg ggc cag cct ggg    1493
Ser Trp Gly Ser Gly Arg Gln Ser Ser Pro Arg Met Gly Gln Pro Gly
    475                 480                 485 cca ggc tcc atg ccg tca aga gct gct tct cac act tca gat ttc aac    1541
Pro Gly Ser Met Pro Ser Arg Ala Ala Ser His Thr Ser Asp Phe Asn
490                 495                 500                 505 ccg aac gct ggc tca gac caa aga gta gtt aat gga ggt gtt ccc tgg    1589
Pro Asn Ala Gly Ser Asp Gln Arg Val Val Asn Gly Gly Val Pro Trp
                510                 515                 520 cca tcg cct tgc cca tct cat tcc tct cgc cca cct tct cgc tac cag    1637
Pro Ser Pro Cys Pro Ser His Ser Ser Arg Pro Pro Ser Arg Tyr Gln
            525                 530                 535 tca ggt ccc aac tct ctt cca cct cgg gca gcc acc cat aca cgg ccg    1685
Ser Gly Pro Asn Ser Leu Pro Pro Arg Ala Ala Thr His Thr Arg Pro
        540                 545                 550 ccc tcc agg ccc ccc tcg agg cca tcc aga ccc ccg tct cac ccc tct    1733
Pro Ser Arg Pro Pro Ser Arg Pro Ser Arg Pro Pro Ser His Pro Ser
    555                 560                 565 gct cat ggt tct cca gct cct gtc tct act atg cct aaa cgc atg tct    1781
Ala His Gly Ser Pro Ala Pro Val Ser Thr Met Pro Lys Arg Met Ser
570                 575                 580                 585 tca gaa gga ccc cca agg atg tct cca aag gca cag cgc cac cct cgg    1829
Ser Glu Gly Pro Pro Arg Met Ser Pro Lys Ala Gln Arg His Pro Arg
                590                 595                 600 aat cac aga gtc tct gct ggg aga ggc tcc atg tct agt ggc cta gaa    1877
Asn His Arg Val Ser Ala Gly Arg Gly Ser Met Ser Ser Gly Leu Glu
            605                 610                 615 ttt gta tcc cac aat ccc cca agt gaa gca gct gct cct cca gtg gca    1925
Phe Val Ser His Asn Pro Pro Ser Glu Ala Ala Ala Pro Pro Val Ala
        620                 625                 630 agg acc agt cct gca ggg gga acg tgg tcc tca gtg gtc agt ggg gtt    1973
Arg Thr Ser Pro Ala Gly Gly Thr Trp Ser Ser Val Val Ser Gly Val
    635                 640                 645 cca agg tta tct ccc aaa act cac aga ccc agg tct ccc agg cag agc    2021
Pro Arg Leu Ser Pro Lys Thr His Arg Pro Arg Ser Pro Arg Gln Ser
650                 655                 660                 665 agc att gga aac tct ccc agc ggg cct gtg ctt gct tct ccc caa gct    2069
Ser Ile Gly Asn Ser Pro Ser Gly Pro Val Leu Ala Ser Pro Gln Ala
                670                 675                 680 ggc atc atc cct gca gaa gcc gtt tcc atg cct gtt ccc gcc gca tct    2117
Gly Ile Ile Pro Ala Glu Ala Val Ser Met Pro Val Pro Ala Ala Ser
            685                 690                 695 ccg act cct gcc agc cct gca tcc aac aga gca ctg acc cca tct att    2165
Pro Thr Pro Ala Ser Pro Ala Ser Asn Arg Ala Leu Thr Pro Ser Ile
        700                 705                 710 gag gca aaa gat tcc agg ctt caa gat cag agg cag aac tct cct gca    2213
Glu Ala Lys Asp Ser Arg Leu Gln Asp Gln Arg Gln Asn Ser Pro Ala
```

```
Glu Ala Lys Asp Ser Arg Leu Gln Asp Gln Arg Gln Asn Ser Pro Ala
    715                 720                 725 ggg agt aaa gaa aat gtt aaa gca agt gaa aca tca cct agc ttt tca    2261
Gly Ser Lys Glu Asn Val Lys Ala Ser Glu Thr Ser Pro Ser Phe Ser
730                 735                 740                 745 aaa gct gac aac aaa ggt atg tca cca gtt gtt tct gaa cac aga aaa    2309
Lys Ala Asp Asn Lys Gly Met Ser Pro Val Val Ser Glu His Arg Lys
                750                 755                 760 cag att gat gac tta aag aag ttt aag aat gat ttt agg tta cag cca    2357
Gln Ile Asp Asp Leu Lys Lys Phe Lys Asn Asp Phe Arg Leu Gln Pro
            765                 770                 775 agc tct aca tct gaa tct atg gat caa cta cta agc aaa aat aga gaa    2405
Ser Ser Thr Ser Glu Ser Met Asp Gln Leu Leu Ser Lys Asn Arg Glu
        780                 785                 790 gga gaa aag tca cga gat ttg att aaa gat aaa acg gaa gca agt gct    2453
Gly Glu Lys Ser Arg Asp Leu Ile Lys Asp Lys Thr Glu Ala Ser Ala
    795                 800                 805 aag gat agt ttc att gac agc agc agc agc agc aac tgt acc agt        2501
Lys Asp Ser Phe Ile Asp Ser Ser Ser Ser Ser Asn Cys Thr Ser
810                 815                 820                 825 ggc agc agc aag acc aac agc cct agc atc tcc cct tcc atg ctt agt    2549
Gly Ser Ser Lys Thr Asn Ser Pro Ser Ile Ser Pro Ser Met Leu Ser
                830                 835                 840 aat gca gag cac aag agg ggg cct gag gtc aca tcc caa ggg gtg cag    2597
Asn Ala Glu His Lys Arg Gly Pro Glu Val Thr Ser Gln Gly Val Gln
            845                 850                 855 act tcc agc cca gcc tgc aaa caa gag aag gat gac aga gaa gag aag    2645
Thr Ser Ser Pro Ala Cys Lys Gln Glu Lys Asp Asp Arg Glu Glu Lys
        860                 865                 870 aaa gac aca aca gag cag gtt agg aaa tcg aca ttg aat ccc aat gca    2693
Lys Asp Thr Thr Glu Gln Val Arg Lys Ser Thr Leu Asn Pro Asn Ala
    875                 880                 885 aag gag ttc aac cct cgt tct ttc tct cag cca aag cct tct act acc    2741
Lys Glu Phe Asn Pro Arg Ser Phe Ser Gln Pro Lys Pro Ser Thr Thr
890                 895                 900                 905 cca acg tca cct cgg cct caa gca caa ccc agc cca tct atg gtg ggt    2789
Pro Thr Ser Pro Arg Pro Gln Ala Gln Pro Ser Pro Ser Met Val Gly
                910                 915                 920 cat cag cag cca gct cca gtg tac act cag cct gtg tgc ttc gca ccc    2837
His Gln Gln Pro Ala Pro Val Tyr Thr Gln Pro Val Cys Phe Ala Pro
            925                 930                 935 aat atg atg tat ccc gtc cca gtg agc ccg ggc gta caa cct tta tac    2885
Asn Met Met Tyr Pro Val Pro Val Ser Pro Gly Val Gln Pro Leu Tyr
        940                 945                 950 cca ata cct atg acg ccc atg cct gtg aac caa gcc aag aca tat aga    2933
Pro Ile Pro Met Thr Pro Met Pro Val Asn Gln Ala Lys Thr Tyr Arg
    955                 960                 965 gca ggt aaa gta cca aat atg ccc caa cag cga caa gac caa cat cat    2981
Ala Gly Lys Val Pro Asn Met Pro Gln Gln Arg Gln Asp Gln His His
970                 975                 980                 985 caa agc acc atg atg cac cca gcc tcc gcg gca ggg cca ccc atc gta    3029
Gln Ser Thr Met Met His Pro Ala Ser Ala Ala Gly Pro Pro Ile Val
                990                 995                 1000 gcc acc ccg ccc gct tac tcc act cag tac gtt gcc tac agc cct cag   3077
Ala Thr Pro Pro Ala Tyr Ser Thr Gln Tyr Val Ala Tyr Ser Pro Gln
            1005                1010                1015 cag ttt ccc aat cag cct ttg gtc cag cat gtg ccg cat tat cag tct   3125
Gln Phe Pro Asn Gln Pro Leu Val Gln His Val Pro His Tyr Gln Ser
        1020                1025                1030
```

```
cag cat cct cat gtg tac agt cct gtc ata caa ggt aat gcc agg atg      3173
Gln His Pro His Val Tyr Ser Pro Val Ile Gln Gly Asn Ala Arg Met
        1035                1040                1045 atg gca cca cca gca cat gct cag cct ggt tta gtg tct tct tca gct      3221
Met Ala Pro Pro Ala His Ala Gln Pro Gly Leu Val Ser Ser Ser Ala
1050                1055                1060                1065 gct cag ttc ggg gct cac gag cag acg cac gcc atg tat gca tgt ccc      3269
Ala Gln Phe Gly Ala His Glu Gln Thr His Ala Met Tyr Ala Cys Pro
                1070                1075                1080 aaa tta cca tac aac aag gag aca agc cct tct ttc tac ttt gcc att      3317
Lys Leu Pro Tyr Asn Lys Glu Thr Ser Pro Ser Phe Tyr Phe Ala Ile
            1085                1090                1095 tcc acc ggc tcc ctc gct cag cag tat gca cat cct aat gcc gcc ctg      3365
Ser Thr Gly Ser Leu Ala Gln Gln Tyr Ala His Pro Asn Ala Ala Leu
        1100                1105                1110 cat cca cat act ccc cat cct cag cct tcg gcc act ccc acc gga cag      3413
His Pro His Thr Pro His Pro Gln Pro Ser Ala Thr Pro Thr Gly Gln
    1115                1120                1125 cag caa agc cag cat ggt gga agt cac cct gca ccc agt cct gtt cag      3461
Gln Gln Ser Gln His Gly Gly Ser His Pro Ala Pro Ser Pro Val Gln
1130                1135                1140                1145 cac cat cag cac cag gct gcc cag gct ctt cat ctg gcc agt cca cag      3509
His His Gln His Gln Ala Ala Gln Ala Leu His Leu Ala Ser Pro Gln
                1150                1155                1160 cag cag tcg gcc att tat cat gcg ggg ctg gca cca aca cca cct tcc      3557
Gln Gln Ser Ala Ile Tyr His Ala Gly Leu Ala Pro Thr Pro Pro Ser
            1165                1170                1175 atg aca cct gcc tct aat aca cag tct cca cag agc agt ttc cca gca      3605
Met Thr Pro Ala Ser Asn Thr Gln Ser Pro Gln Ser Ser Phe Pro Ala
        1180                1185                1190 gca caa cag aca gtc ttc acc atc cac cct tct cat gtt cag ccg gca      3653
Ala Gln Gln Thr Val Phe Thr Ile His Pro Ser His Val Gln Pro Ala
    1195                1200                1205 tac acc acc cca ccc cac atg gcc cac gta cct cag gct cat gta cag      3701
Tyr Thr Thr Pro Pro His Met Ala His Val Pro Gln Ala His Val Gln
1210                1215                1220                1225 tca gga atg gtt cct tct cat cca act gcc cat gcg cca atg atg cta      3749
Ser Gly Met Val Pro Ser His Pro Thr Ala His Ala Pro Met Met Leu
                1230                1235                1240 atg acg aca cag cca ccc ggt ccc aag gcc gcc ctc gct caa agt gca      3797
Met Thr Thr Gln Pro Pro Gly Pro Lys Ala Ala Leu Ala Gln Ser Ala
            1245                1250                1255 cta cag ccc att cca gtt tcg aca aca gcg cat ttc cct tat atg acg      3845
Leu Gln Pro Ile Pro Val Ser Thr Thr Ala His Phe Pro Tyr Met Thr
        1260                1265                1270 cac cct tca gta caa gcc cac cac caa cag cag ttg taa ggctgccttg      3894
His Pro Ser Val Gln Ala His His Gln Gln Gln Leu  *
    1275                1280                1285 gaggaaccga aaggccaaat cccttcttcc cttctctgct tctgccaacc ggaagcacag   3954
aaaactagaa cttcattgat tttgtttttt aaaagataca ctgatttaac atctgatagg   4014
aatgctaaca gctcacttgc agtggaggat gttttggacc gagtagaggc atgtagggac   4074
ttgtggctgt tccataattc catgtgctgt tgcagggtcc tgcaagtacc cagctctgct   4134
tgctgaaact ggaagttatt tatttttttaa tggcccttga gagtcatgaa cacatcagct   4194
agcaacagaa gtaacaagag tgattcttgc t                                  4225

<210> SEQ ID NO 4
<211> LENGTH: 1285
```

```
<212> TYPE: PRT
<213> ORGANISM: Mus musculus
<220> FEATURE:
<221> NAME/KEY: VARIANT
<222> LOCATION: 66
<223> OTHER INFORMATION: Xaa=Pro

<400> SEQUENCE: 4
```

Met Arg Ser Ser Thr Ala Ala Val Gln Arg Pro Ala Ala Gly Asp Pro
 1               5                  10                  15

Glu Pro Arg Arg Pro Ala Gly Trp Ala Ala Arg Arg Ser Leu Pro Arg
                20                  25                  30

Thr Ala Arg Arg Gly Gly Arg Gly Ala Val Ala Tyr Pro Ser Ala
            35                  40                  45

Gly Pro Pro Arg Gly Pro Gly Ala Pro Arg Gly Pro Arg Ser
 50                  55                  60

Pro Xaa Cys Ala Ser Asp Cys Phe Gly Ser Asn Gly His Gly Ala Ser
65                   70                  75                  80

Arg Pro Gly Ser Arg Arg Leu Leu Gly Val Cys Gly Pro Pro Arg Pro
                85                  90                  95

Phe Val Val Val Leu Leu Ala Leu Ala Pro Ala Ala Thr Pro Ala Arg
                100                 105                 110

Ala Cys Pro Pro Gly Val Arg Ala Ser Pro Pro Arg Ser Gly Val Ser
            115                 120                 125

Ser Ser Ala Arg Pro Ala Pro Gly Cys Pro Arg Pro Ala Cys Glu Pro
130                 135                 140

Val Tyr Gly Pro Leu Thr Met Ser Leu Lys Pro Gln Pro Gln Pro Pro
145                 150                 155                 160

Ala Pro Ala Thr Gly Arg Lys Pro Gly Gly Gly Leu Leu Ser Ser Pro
                165                 170                 175

Gly Ala Ala Pro Ala Ser Ala Ala Val Thr Ser Ala Ser Val Val Pro
            180                 185                 190

Ala Pro Ala Ala Pro Val Ala Ser Ser Ala Ala Ala Gly Gly Gly
            195                 200                 205

Arg Pro Gly Leu Gly Arg Gly Arg Asn Ser Ser Lys Gly Leu Pro Gln
210                 215                 220

Pro Thr Ile Ser Phe Asp Gly Ile Tyr Ala Asn Val Arg Met Val His
225                 230                 235                 240

Ile Leu Thr Ser Val Val Gly Ser Lys Cys Glu Val Gln Val Lys Asn
                245                 250                 255

Gly Gly Ile Tyr Glu Gly Val Phe Lys Thr Tyr Ser Pro Lys Cys Asp
            260                 265                 270

Leu Val Leu Asp Ala Ala His Glu Lys Ser Thr Glu Ser Ser Gly
            275                 280                 285

Pro Lys Arg Glu Glu Ile Met Glu Ser Val Leu Phe Lys Cys Ser Asp
290                 295                 300

Phe Val Val Val Gln Phe Lys Asp Thr Asp Ser Ser Tyr Ala Arg Arg
305                 310                 315                 320

Asp Ala Phe Thr Asp Ser Ala Leu Ser Ala Lys Val Asn Gly Glu His
                325                 330                 335

Lys Glu Lys Asp Leu Glu Pro Trp Asp Ala Gly Glu Leu Thr Ala Ser
            340                 345                 350

Glu Glu Leu Glu Leu Glu Asn Asp Val Ser Asn Gly Trp Asp Pro Asn
            355                 360                 365

Asp Met Phe Arg Tyr Asn Glu Glu Asn Tyr Gly Val Val Ser Thr Tyr

-continued

```
            370                 375                 380
Asp Ser Ser Leu Ser Ser Tyr Thr Val Pro Leu Glu Arg Asp Asn Ser
385                 390                 395                 400

Glu Glu Phe Leu Lys Arg Glu Ala Arg Ala Asn Gln Leu Ala Glu Glu
                405                 410                 415

Ile Glu Ser Ser Ala Gln Tyr Lys Ala Arg Val Ala Leu Glu Asn Asp
                420                 425                 430

Asp Arg Ser Glu Glu Lys Tyr Thr Ala Val Gln Arg Asn Cys Ser
                435                 440                 445

Asp Arg Glu Gly His Gly Pro Asn Thr Arg Asp Asn Lys Tyr Ile Pro
450                 455                 460

Pro Gly Gln Arg Asn Arg Glu Val Leu Ser Trp Gly Ser Gly Arg Gln
465                 470                 475                 480

Ser Ser Pro Arg Met Gly Gln Pro Gly Pro Gly Ser Met Pro Ser Arg
                485                 490                 495

Ala Ala Ser His Thr Ser Asp Phe Asn Pro Asn Ala Gly Ser Asp Gln
                500                 505                 510

Arg Val Val Asn Gly Gly Val Pro Trp Pro Ser Pro Cys Pro Ser His
                515                 520                 525

Ser Ser Arg Pro Pro Ser Arg Tyr Gln Ser Gly Pro Asn Ser Leu Pro
                530                 535                 540

Pro Arg Ala Ala Thr His Thr Arg Pro Pro Ser Arg Pro Pro Ser Arg
545                 550                 555                 560

Pro Ser Arg Pro Pro Ser His Pro Ser Ala His Gly Ser Pro Ala Pro
                565                 570                 575

Val Ser Thr Met Pro Lys Arg Met Ser Ser Glu Gly Pro Pro Arg Met
                580                 585                 590

Ser Pro Lys Ala Gln Arg His Pro Arg Asn His Arg Val Ser Ala Gly
                595                 600                 605

Arg Gly Ser Met Ser Ser Gly Leu Glu Phe Val Ser His Asn Pro Pro
                610                 615                 620

Ser Glu Ala Ala Ala Pro Pro Val Ala Arg Thr Ser Pro Ala Gly Gly
625                 630                 635                 640

Thr Trp Ser Ser Val Val Ser Gly Val Pro Arg Leu Ser Pro Lys Thr
                645                 650                 655

His Arg Pro Arg Ser Pro Arg Gln Ser Ser Ile Gly Asn Ser Pro Ser
                660                 665                 670

Gly Pro Val Leu Ala Ser Pro Gln Ala Gly Ile Ile Pro Ala Glu Ala
                675                 680                 685

Val Ser Met Pro Val Pro Ala Ala Ser Pro Thr Pro Ala Ser Pro Ala
                690                 695                 700

Ser Asn Arg Ala Leu Thr Pro Ser Ile Glu Ala Lys Asp Ser Arg Leu
705                 710                 715                 720

Gln Asp Gln Arg Gln Asn Ser Pro Ala Gly Ser Lys Glu Asn Val Lys
                725                 730                 735

Ala Ser Glu Thr Ser Pro Ser Phe Ser Lys Ala Asp Asn Lys Gly Met
                740                 745                 750

Ser Pro Val Val Ser Glu His Arg Lys Gln Ile Asp Asp Leu Lys Lys
                755                 760                 765

Phe Lys Asn Asp Phe Arg Leu Gln Pro Ser Ser Thr Ser Glu Ser Met
                770                 775                 780

Asp Gln Leu Leu Ser Lys Asn Arg Glu Gly Glu Lys Ser Arg Asp Leu
785                 790                 795                 800
```

```
Ile Lys Asp Lys Thr Glu Ala Ser Ala Lys Asp Ser Phe Ile Asp Ser
            805                 810                 815

Ser Ser Ser Ser Ser Asn Cys Thr Ser Gly Ser Ser Lys Thr Asn Ser
            820                 825                 830

Pro Ser Ile Ser Pro Ser Met Leu Ser Asn Ala Glu His Lys Arg Gly
            835                 840                 845

Pro Glu Val Thr Ser Gln Gly Val Gln Thr Ser Ser Pro Ala Cys Lys
            850                 855                 860

Gln Glu Lys Asp Asp Arg Glu Glu Lys Lys Asp Thr Thr Glu Gln Val
865                 870                 875                 880

Arg Lys Ser Thr Leu Asn Pro Asn Ala Lys Glu Phe Asn Pro Arg Ser
            885                 890                 895

Phe Ser Gln Pro Lys Pro Ser Thr Thr Pro Thr Ser Pro Arg Pro Gln
            900                 905                 910

Ala Gln Pro Ser Pro Ser Met Val Gly His Gln Gln Pro Ala Pro Val
            915                 920                 925

Tyr Thr Gln Pro Val Cys Phe Ala Pro Asn Met Met Tyr Pro Val Pro
            930                 935                 940

Val Ser Pro Gly Val Gln Pro Leu Tyr Pro Ile Pro Met Thr Pro Met
945                 950                 955                 960

Pro Val Asn Gln Ala Lys Thr Tyr Arg Ala Gly Lys Val Pro Asn Met
            965                 970                 975

Pro Gln Gln Arg Gln Asp Gln His His Gln Ser Thr Met Met His Pro
            980                 985                 990

Ala Ser Ala Ala Gly Pro Pro Ile Val Ala Thr Pro Pro Ala Tyr Ser
            995                 1000                1005

Thr Gln Tyr Val Ala Tyr Ser Pro Gln Gln Phe Pro Asn Gln Pro Leu
            1010                1015                1020

Val Gln His Val Pro His Tyr Gln Ser Gln His Pro His Val Tyr Ser
1025                1030                1035                1040

Pro Val Ile Gln Gly Asn Ala Arg Met Met Ala Pro Pro Ala His Ala
            1045                1050                1055

Gln Pro Gly Leu Val Ser Ser Ala Ala Gln Phe Gly Ala His Glu
            1060                1065                1070

Gln Thr His Ala Met Tyr Ala Cys Pro Lys Leu Pro Tyr Asn Lys Glu
            1075                1080                1085

Thr Ser Pro Ser Phe Tyr Phe Ala Ile Ser Thr Gly Ser Leu Ala Gln
            1090                1095                1100

Gln Tyr Ala His Pro Asn Ala Ala Leu His Pro His Thr Pro His Pro
1105                1110                1115                1120

Gln Pro Ser Ala Thr Pro Thr Gly Gln Gln Gln Ser Gln His Gly Gly
            1125                1130                1135

Ser His Pro Ala Pro Ser Pro Val Gln His His Gln His Gln Ala Ala
            1140                1145                1150

Gln Ala Leu His Leu Ala Ser Pro Gln Gln Gln Ser Ala Ile Tyr His
            1155                1160                1165

Ala Gly Leu Ala Pro Thr Pro Pro Ser Met Thr Pro Ala Ser Asn Thr
            1170                1175                1180

Gln Ser Pro Gln Ser Ser Phe Pro Ala Ala Gln Gln Thr Val Phe Thr
1185                1190                1195                1200

Ile His Pro Ser His Val Gln Pro Ala Tyr Thr Thr Pro Pro His Met
            1205                1210                1215
```

```
Ala His Val Pro Gln Ala His Val Gln Ser Gly Met Val Pro Ser His
        1220                1225                1230

Pro Thr Ala His Ala Pro Met Met Leu Met Thr Thr Gln Pro Pro Gly
        1235                1240                1245

Pro Lys Ala Ala Leu Ala Gln Ser Ala Leu Gln Pro Ile Pro Val Ser
        1250                1255                1260

Thr Thr Ala His Phe Pro Tyr Met Thr His Pro Ser Val Gln Ala His
1265                1270                1275                1280

His Gln Gln Gln Leu
            1285

<210> SEQ ID NO 5
<211> LENGTH: 4481
<212> TYPE: DNA
<213> ORGANISM: Homo sapiens
<220> FEATURE:
<221> NAME/KEY: CDS
<222> LOCATION: (163)...(4101)

<400> SEQUENCE: 5 accccccgaga aagcaaccca gcgcgccgcc cgctcctcac gtgtccctcc cggccccggg      60
gccacctcac gttctgcttc cgtctgaccc ctccgacttc cggtaaagag tccctatccg     120
cacctccgct cccaccccggc gcctcggcgc gcccgccctc cg atg cgc tca gcg       174
                                                   Met Arg Ser Ala
                                                     1 gcc gca gct cct cgg agt ccc gcg gtg gcc acc gag tct cgc cgc ttc       222
Ala Ala Ala Pro Arg Ser Pro Ala Val Ala Thr Glu Ser Arg Arg Phe
  5                  10                  15                  20 gcc gca gcc agg tgg ccc ggg tgg cgc tcg ctc cag cgg ccg gcg cgg       270
Ala Ala Ala Arg Trp Pro Gly Trp Arg Ser Leu Gln Arg Pro Ala Arg
             25                  30                  35 cgg agc ggg cgg ggc ggt ggc gcg gcc ccg gga ccg tat ccc tcc           318
Arg Ser Gly Arg Gly Gly Gly Ala Ala Pro Gly Pro Tyr Pro Ser
         40                  45                  50 gcc gcc cct ccc ccg ccc ggc ccc ggc ccc cct ccc tcc cgg cag agc       366
Ala Ala Pro Pro Pro Pro Gly Pro Gly Pro Pro Ser Arg Gln Ser
     55                  60                      65 tcg cct ccc tcc gcc tca gac tgt ttt ggt agc aac ggc aac ggc ggc       414
Ser Pro Pro Ser Ala Ser Asp Cys Phe Gly Ser Asn Gly Asn Gly Gly
 70                  75                  80 ggc gcg ttt cgg ccc ggc tcc cgg cgg ctc ctt ggt ctc ggc ggg cct       462
Gly Ala Phe Arg Pro Gly Ser Arg Arg Leu Leu Gly Leu Gly Gly Pro
 85                  90                  95                 100 ccc cgc ccc ttc gtc gtc gtc ctt ctc ccc ctc gcc agc ccg ggc gcc       510
Pro Arg Pro Phe Val Val Val Leu Leu Pro Leu Ala Ser Pro Gly Ala
                105                 110                 115 cct ccg gcc gcg cca acc cgc gcc tcc ccg ctc ggc gcc cgt gcg tcc       558
Pro Pro Ala Ala Pro Thr Arg Ala Ser Pro Leu Gly Ala Arg Ala Ser
            120                 125                 130 ccg ccg cgt tcc ggc gtc tcc ttg gcg cgc ccg gct ccc ggc tgt ccc       606
Pro Pro Arg Ser Gly Val Ser Leu Ala Arg Pro Ala Pro Gly Cys Pro
        135                 140                 145 cgc ccg gcg tgc gag ccg gtg tat ggg ccc ctc acc atg tcg ctg aag       654
Arg Pro Ala Cys Glu Pro Val Tyr Gly Pro Leu Thr Met Ser Leu Lys
    150                 155                 160 ccc cag cag cag cag cag cag cag cag caa cag cag cag caa cag           702
Pro Gln Gln Gln Gln Gln Gln Gln Gln Gln Gln Gln Gln Gln Gln
165                 170                 175                 180 cag cag cag cag cag cag cag ccg ccg ccc gcg gct gcc aat gtc cgc       750
```

```
Gln Gln Gln Gln Gln Gln Gln Pro Pro Pro Ala Ala Ala Asn Val Arg
                185                 190                 195 aag ccc ggc ggc agc ggc ctt cta gcg tcg ccc gcc gcc gcg cct tcg      798
Lys Pro Gly Gly Ser Gly Leu Leu Ala Ser Pro Ala Ala Ala Pro Ser
            200                 205                 210 ccg tcc tcg tcc tcg gtc tcc tcg tcc tcg gcc acg gct ccc tcc tcg      846
Pro Ser Ser Ser Ser Val Ser Ser Ser Ser Ala Thr Ala Pro Ser Ser
            215                 220                 225 gtg gtc gcg gcg acc tcc ggc ggc ggg agg ccc ggc ctg ggc aga ggt      894
Val Val Ala Ala Thr Ser Gly Gly Gly Arg Pro Gly Leu Gly Arg Gly
            230                 235                 240 cga aac agt aac aaa gga ctg cct cag tct acg att tct ttt gat gga      942
Arg Asn Ser Asn Lys Gly Leu Pro Gln Ser Thr Ile Ser Phe Asp Gly
245                 250                 255                 260 atc tat gca aat atg agg atg gtt cat ata ctt aca tca gtt gtt ggc      990
Ile Tyr Ala Asn Met Arg Met Val His Ile Leu Thr Ser Val Val Gly
                265                 270                 275 tcc aaa tgt gaa gta caa gtg aaa aat gga ggt ata tat gaa gga gtt     1038
Ser Lys Cys Glu Val Gln Val Lys Asn Gly Gly Ile Tyr Glu Gly Val
            280                 285                 290 ttt aaa act tac agt ccg aag tgt gat ttg gta ctt gat gcc gca cat     1086
Phe Lys Thr Tyr Ser Pro Lys Cys Asp Leu Val Leu Asp Ala Ala His
            295                 300                 305 gag aaa agt aca gaa tcc agt tcg ggg ccg aaa cgt gaa gaa ata atg     1134
Glu Lys Ser Thr Glu Ser Ser Ser Gly Pro Lys Arg Glu Glu Ile Met
310                 315                 320 gag agt att ttg ttc aaa tgt tca gac ttt gtt gtg gta cag ttt aaa     1182
Glu Ser Ile Leu Phe Lys Cys Ser Asp Phe Val Val Val Gln Phe Lys
325                 330                 335                 340 gat atg gac tcc agt tat gca aaa aga gat gct ttt act gac tct gct     1230
Asp Met Asp Ser Ser Tyr Ala Lys Arg Asp Ala Phe Thr Asp Ser Ala
            345                 350                 355 atc agt gct aaa gtg aat ggc gaa cac aaa gag aag gac ctg gag ccc     1278
Ile Ser Ala Lys Val Asn Gly Glu His Lys Glu Lys Asp Leu Glu Pro
            360                 365                 370 tgg gat gca ggt gaa ctc aca gcc aat gag gaa ctt gag gct ttg gaa     1326
Trp Asp Ala Gly Glu Leu Thr Ala Asn Glu Glu Leu Glu Ala Leu Glu
            375                 380                 385 aat gac gta tct aat gga tgg gat ccc aat gat atg ttt cga tat aat     1374
Asn Asp Val Ser Asn Gly Trp Asp Pro Asn Asp Met Phe Arg Tyr Asn
            390                 395                 400 gaa gaa aat tat ggt gta gtg tct acg tat gat agc agt tta tct tcg     1422
Glu Glu Asn Tyr Gly Val Val Ser Thr Tyr Asp Ser Ser Leu Ser Ser
405                 410                 415                 420 tat aca gtg ccc tta gaa aga gat aac tca gaa gaa ttt tta aaa cgg     1470
Tyr Thr Val Pro Leu Glu Arg Asp Asn Ser Glu Glu Phe Leu Lys Arg
            425                 430                 435 gaa gca agg gca aac cag tta gca gaa gaa att gag tca agt gcc cag     1518
Glu Ala Arg Ala Asn Gln Leu Ala Glu Glu Ile Glu Ser Ser Ala Gln
            440                 445                 450 tac aaa gct cga gtg gcc ctg gaa aat gat gat agg agt gag gaa gaa     1566
Tyr Lys Ala Arg Val Ala Leu Glu Asn Asp Asp Arg Ser Glu Glu Glu
            455                 460                 465 aaa tac aca gca gtt cag aga aat tcc agt gaa cgt gag ggg cac agc     1614
Lys Tyr Thr Ala Val Gln Arg Asn Ser Ser Glu Arg Glu Gly His Ser
470                 475                 480 ata aac act agg gaa aat aaa tat att cct cct gga caa aga aat aga     1662
Ile Asn Thr Arg Glu Asn Lys Tyr Ile Pro Pro Gly Gln Arg Asn Arg
485                 490                 495                 500
```

```
                                                     -continued gaa gtc ata tcc tgg gga agt ggg aga cag aat tca ccg cgt atg ggc    1710
Glu Val Ile Ser Trp Gly Ser Gly Arg Gln Asn Ser Pro Arg Met Gly
            505                 510                 515 cag cct gga tcg ggc tcc atg cca tca aga tcc act tct cac act tca    1758
Gln Pro Gly Ser Gly Ser Met Pro Ser Arg Ser Thr Ser His Thr Ser
        520                 525                 530 gat ttc aac ccg aat tct ggt tca gac caa aga gta gtt aat gga ggt    1806
Asp Phe Asn Pro Asn Ser Gly Ser Asp Gln Arg Val Val Asn Gly Gly
        535                 540                 545 gtt ccc tgg cca tcg cct tgc cca tct cct tcc tct cgc cca cct tct    1854
Val Pro Trp Pro Ser Pro Cys Pro Ser Pro Ser Ser Arg Pro Pro Ser
    550                 555                 560 cgc tac cag tca ggt ccc aac tct ctt cca cct cgg gca gcc acc cct    1902
Arg Tyr Gln Ser Gly Pro Asn Ser Leu Pro Pro Arg Ala Ala Thr Pro
565                 570                 575                 580 aca cgg ccg ccc tcc agg ccc ccc tcg cgg cca tcc aga ccc ccg tct    1950
Thr Arg Pro Pro Ser Arg Pro Pro Ser Arg Pro Ser Arg Pro Pro Ser
                585                 590                 595 cac ccc tct gct cat ggt tct cca gct cct gtc tct act atg cct aaa    1998
His Pro Ser Ala His Gly Ser Pro Ala Pro Val Ser Thr Met Pro Lys
            600                 605                 610 cgc atg tct tca gaa ggg cct cca agg atg tcc cca aag gcc cag cga    2046
Arg Met Ser Ser Glu Gly Pro Pro Arg Met Ser Pro Lys Ala Gln Arg
        615                 620                 625 cat cct cga aat cac aga gtt tct gct ggg agg ggt tcc ata tcc agt    2094
His Pro Arg Asn His Arg Val Ser Ala Gly Arg Gly Ser Ile Ser Ser
        630                 635                 640 ggc cta gaa ttt gta tcc cac aac cca ccc agt gaa gca gct act cct    2142
Gly Leu Glu Phe Val Ser His Asn Pro Pro Ser Glu Ala Ala Thr Pro
645                 650                 655                 660 cca gta gca agg acc agt ccc tcg ggg gga acg tgg tca tca gtg gtc    2190
Pro Val Ala Arg Thr Ser Pro Ser Gly Gly Thr Trp Ser Ser Val Val
                665                 670                 675 agt ggg gtt cca aga tta tcc cct aaa act cat aga ccc agg tct ccc    2238
Ser Gly Val Pro Arg Leu Ser Pro Lys Thr His Arg Pro Arg Ser Pro
            680                 685                 690 aga cag aac agt att gga aat acc ccc agt ggg cca gtt ctt gct tct    2286
Arg Gln Asn Ser Ile Gly Asn Thr Pro Ser Gly Pro Val Leu Ala Ser
        695                 700                 705 ccc caa gct ggt att att cca act gaa gct gtt gcc atg cct att cca    2334
Pro Gln Ala Gly Ile Ile Pro Thr Glu Ala Val Ala Met Pro Ile Pro
    710                 715                 720 gct gca tct cct acg cct gct agt cct gca tcg aac aga gct gtt acc    2382
Ala Ala Ser Pro Thr Pro Ala Ser Pro Ala Ser Asn Arg Ala Val Thr
725                 730                 735                 740 cct tct agt gag gct aaa gat tcc agg ctt caa gat cag agg cag aac    2430
Pro Ser Ser Glu Ala Lys Asp Ser Arg Leu Gln Asp Gln Arg Gln Asn
                745                 750                 755 tct cct gca ggg aat aaa gaa aat att aaa ccc aat gaa aca tca cct    2478
Ser Pro Ala Gly Asn Lys Glu Asn Ile Lys Pro Asn Glu Thr Ser Pro
            760                 765                 770 agc ttc tca aaa gct gaa aac aaa ggt ata tca cca gtt gtt tct gaa    2526
Ser Phe Ser Lys Ala Glu Asn Lys Gly Ile Ser Pro Val Val Ser Glu
        775                 780                 785 cat aga aaa cag att gat gat tta aag aaa ttt aag aat gat ttt agg    2574
His Arg Lys Gln Ile Asp Asp Leu Lys Lys Phe Lys Asn Asp Phe Arg
    790                 795                 800 tta cag cca agt tct act tct gaa tct atg gat caa cta cta aac aaa    2622
Leu Gln Pro Ser Ser Thr Ser Glu Ser Met Asp Gln Leu Leu Asn Lys
805                 810                 815                 820
```

```
aat aga gag gga gaa aaa tca aga gat ttg atc aaa gac aaa att gaa    2670
Asn Arg Glu Gly Glu Lys Ser Arg Asp Leu Ile Lys Asp Lys Ile Glu
                825                 830                 835 cca agt gct aag gat tct ttc att gaa aat agc agc agc aac tgt acc    2718
Pro Ser Ala Lys Asp Ser Phe Ile Glu Asn Ser Ser Ser Asn Cys Thr
            840                 845                 850 agt ggc agc agc aag ccg aat agc ccc agc att tcc cct tca ata ctt    2766
Ser Gly Ser Ser Lys Pro Asn Ser Pro Ser Ile Ser Pro Ser Ile Leu
        855                 860                 865 agt aac acg gag cac aag agg gga cct gag gtc act tcc caa ggg gtt    2814
Ser Asn Thr Glu His Lys Arg Gly Pro Glu Val Thr Ser Gln Gly Val
    870                 875                 880 cag act tcc agc cca gca tgt aaa caa gag aaa gac gat aag gaa gag    2862
Gln Thr Ser Ser Pro Ala Cys Lys Gln Glu Lys Asp Asp Lys Glu Glu
885                 890                 895                 900 aag aaa gac gca gct gag caa gtt agg aaa tca aca ttg aat ccc aat    2910
Lys Lys Asp Ala Ala Glu Gln Val Arg Lys Ser Thr Leu Asn Pro Asn
                905                 910                 915 gca aag gag ttc aac cca cgt tcc ttc tct cag cca aag cct tct act    2958
Ala Lys Glu Phe Asn Pro Arg Ser Phe Ser Gln Pro Lys Pro Ser Thr
            920                 925                 930 acc cca act tca cct cgg cct caa gca caa cct agc cca tct atg gtg    3006
Thr Pro Thr Ser Pro Arg Pro Gln Ala Gln Pro Ser Pro Ser Met Val
        935                 940                 945 ggt cat caa cag cca act cca gtt tat act cag cct gtt tgt ttt gca    3054
Gly His Gln Gln Pro Thr Pro Val Tyr Thr Gln Pro Val Cys Phe Ala
    950                 955                 960 cca aat atg atg tat cca gtc cca gtg agc cca ggc gtg caa cct tta    3102
Pro Asn Met Met Tyr Pro Val Pro Val Ser Pro Gly Val Gln Pro Leu
965                 970                 975                 980 tac cca ata cct atg acg ccc atg cca gtg aat caa gcc aag aca tat    3150
Tyr Pro Ile Pro Met Thr Pro Met Pro Val Asn Gln Ala Lys Thr Tyr
                985                 990                 995 aga gca gta cca aat atg ccc caa cag cgg caa gac cag cat cat cag    3198
Arg Ala Val Pro Asn Met Pro Gln Gln Arg Gln Asp Gln His His Gln
            1000                1005                1010 agt gcc atg atg cac cca gcg tca gca gcg ggc cca ccg att gca gcc    3246
Ser Ala Met Met His Pro Ala Ser Ala Ala Gly Pro Pro Ile Ala Ala
        1015                1020                1025 acc cca cca gct tac tcc acg caa tat gtt gcc tac agt cct cag cag    3294
Thr Pro Pro Ala Tyr Ser Thr Gln Tyr Val Ala Tyr Ser Pro Gln Gln
    1030                1035                1040 ttc cca aat cag ccc ctt gtt cag cat gtg cca cat tat cag tct cag    3342
Phe Pro Asn Gln Pro Leu Val Gln His Val Pro His Tyr Gln Ser Gln
1045                1050                1055                1060 cat cct cat gtc tat agt cct gta ata cag ggt aat gct aga atg atg    3390
His Pro His Val Tyr Ser Pro Val Ile Gln Gly Asn Ala Arg Met Met
                1065                1070                1075 gca cca cca aca cac gcc cag cct ggt tta gta tct tct tca gca act    3438
Ala Pro Pro Thr His Ala Gln Pro Gly Leu Val Ser Ser Ser Ala Thr
            1080                1085                1090 cag tac ggg gct cat gag cag acg cat gcg atg tat gca tgt ccc aaa    3486
Gln Tyr Gly Ala His Glu Gln Thr His Ala Met Tyr Ala Cys Pro Lys
        1095                1100                1105 tta cca tac aac aag gag aca agc cct tct ttc tac ttt gcc att tcc    3534
Leu Pro Tyr Asn Lys Glu Thr Ser Pro Ser Phe Tyr Phe Ala Ile Ser
    1110                1115                1120 acg ggc tcc ctt gct cag cag tat gcg cac cct aac gct acc ctg cac    3582
Thr Gly Ser Leu Ala Gln Gln Tyr Ala His Pro Asn Ala Thr Leu His
```

|  |  |
|---|---|
| cca cat act cca cac cct cag cct tca gct acc ccc act gga cag cag<br>Pro His Thr Pro His Pro Gln Pro Ser Ala Thr Pro Thr Gly Gln Gln<br>                1145                          1150                        1155 | 3630 |
| caa agc caa cat ggt gga agt cat cct gca ccc agt cct gtt cag cac<br>Gln Ser Gln His Gly Gly Ser His Pro Ala Pro Ser Pro Val Gln His<br>                1160                        1165                        1170 | 3678 |
| cat cag cac cag gcc gcc cag gct ctc cat ctg gcc agt cca cag cag<br>His Gln His Gln Ala Ala Gln Ala Leu His Leu Ala Ser Pro Gln Gln<br>          1175                        1180                        1185 | 3726 |
| cag tca gcc att tac cac gcg ggg ctt gcg cca act cca ccc tcc atg<br>Gln Ser Ala Ile Tyr His Ala Gly Leu Ala Pro Thr Pro Pro Ser Met<br>         1190                        1195                        1200 | 3774 |
| aca cct gcc tcc aac acg cag tcg cca cag aat agt ttc cca gca gca<br>Thr Pro Ala Ser Asn Thr Gln Ser Pro Gln Asn Ser Phe Pro Ala Ala<br>1205                        1210                        1215                        1220 | 3822 |
| caa cag act gtc ttt acg atc cat cct tct cac gtt cag ccg gcg tat<br>Gln Gln Thr Val Phe Thr Ile His Pro Ser His Val Gln Pro Ala Tyr<br>                1225                        1230                        1235 | 3870 |
| acc aac cca ccc cac atg gcc cac gta cct cag gct cat gta cag tca<br>Thr Asn Pro Pro His Met Ala His Val Pro Gln Ala His Val Gln Ser<br>          1240                        1245                        1250 | 3918 |
| gga atg gtt cct tct cat cca act gcc cat gcg cca atg atg cta atg<br>Gly Met Val Pro Ser His Pro Thr Ala His Ala Pro Met Met Leu Met<br>         1255                        1260                        1265 | 3966 |
| acg aca cag cca ccc ggc ggt ccc cag gcc gcc ctc gct caa agt gca<br>Thr Thr Gln Pro Pro Gly Gly Pro Gln Ala Ala Leu Ala Gln Ser Ala<br>         1270                        1275                        1280 | 4014 |
| cta cag ccc att cca gtc tcg aca aca gcg cat ttc ccc tat atg acg<br>Leu Gln Pro Ile Pro Val Ser Thr Thr Ala His Phe Pro Tyr Met Thr<br>1285                        1290                        1295                        1300 | 4062 |
| cac cct tca gta caa gcc cac cac caa cag cag ttg taa ggctgccctg<br>His Pro Ser Val Gln Ala His His Gln Gln Gln Leu  \*<br>                1305                        1310 | 4111 |
| gaggaaccga aaggccaaat tccctcctcc cttctactgc ttctaccaac tggaagcaca | 4171 |
| gaaaactaga atttcattta ttttgttttt aaaatatata tgttgatttc ttgtaacatc | 4231 |
| caataggaat gctaacagtt cacttgcagt ggaagatact tggaccgagt agaggcattt | 4291 |
| aggaacttgg gggctattcc ataattccat atgctgtttc agagtcccgc aggtacccca | 4351 |
| gctctgcttg ccgaaactgg aagttattta tttttttaata accccttgaaa gtcatgaaca | 4411 |
| catcagctag caaaagaagt aacaagagtg attcttgctg ctattactgc taaaaaaaaa | 4471 |
| aaaaaaaaaa | 4481 |

```
<210> SEQ ID NO 6
<211> LENGTH: 1312
<212> TYPE: PRT
<213> ORGANISM: Homo sapiens

<400> SEQUENCE: 6
```

Met Arg Ser Ala Ala Ala Ala Pro Arg Ser Pro Ala Val Ala Thr Glu
 1               5                   10                  15

Ser Arg Arg Phe Ala Ala Ala Arg Trp Pro Gly Trp Arg Ser Leu Gln
                20                  25                  30

Arg Pro Ala Arg Arg Ser Gly Arg Gly Gly Gly Ala Ala Pro Gly
            35                  40                  45

Pro Tyr Pro Ser Ala Ala Pro Pro Pro Gly Pro Gly Pro Pro Pro
        50                  55                  60

```
Ser Arg Gln Ser Ser Pro Pro Ser Ala Ser Asp Cys Phe Gly Ser Asn
 65                  70                  75                  80

Gly Asn Gly Gly Gly Ala Phe Arg Pro Gly Ser Arg Arg Leu Leu Gly
                 85                  90                  95

Leu Gly Gly Pro Pro Arg Pro Phe Val Val Leu Leu Pro Leu Ala
            100                 105                 110

Ser Pro Gly Ala Pro Pro Ala Ala Pro Thr Arg Ala Ser Pro Leu Gly
            115                 120                 125

Ala Arg Ala Ser Pro Pro Arg Ser Gly Val Ser Leu Ala Arg Pro Ala
        130                 135                 140

Pro Gly Cys Pro Arg Pro Ala Cys Glu Pro Val Tyr Gly Pro Leu Thr
145                 150                 155                 160

Met Ser Leu Lys Pro Gln Gln Gln Gln Gln Gln Gln Gln Gln Gln
                165                 170                 175

Gln Gln Gln Gln Gln Gln Gln Gln Gln Gln Pro Pro Ala Ala
            180                 185                 190

Ala Asn Val Arg Lys Pro Gly Gly Ser Gly Leu Leu Ala Ser Pro Ala
        195                 200                 205

Ala Ala Pro Ser Pro Ser Ser Ser Val Ser Ser Ser Ser Ala Thr
210                 215                 220

Ala Pro Ser Ser Val Val Ala Ala Thr Ser Gly Gly Arg Pro Gly
225                 230                 235                 240

Leu Gly Arg Gly Arg Asn Ser Asn Lys Gly Leu Pro Gln Ser Thr Ile
                245                 250                 255

Ser Phe Asp Gly Ile Tyr Ala Asn Met Arg Met Val His Ile Leu Thr
            260                 265                 270

Ser Val Val Gly Ser Lys Cys Glu Val Gln Val Lys Asn Gly Gly Ile
        275                 280                 285

Tyr Glu Gly Val Phe Lys Thr Tyr Ser Pro Lys Cys Asp Leu Val Leu
290                 295                 300

Asp Ala Ala His Glu Lys Ser Thr Glu Ser Ser Gly Pro Lys Arg
305                 310                 315                 320

Glu Glu Ile Met Glu Ser Ile Leu Phe Lys Cys Ser Asp Phe Val Val
                325                 330                 335

Val Gln Phe Lys Asp Met Asp Ser Ser Tyr Ala Lys Arg Asp Ala Phe
            340                 345                 350

Thr Asp Ser Ala Ile Ser Ala Lys Val Asn Gly Glu His Lys Glu Lys
        355                 360                 365

Asp Leu Glu Pro Trp Asp Ala Gly Glu Leu Thr Ala Asn Glu Glu Leu
370                 375                 380

Glu Ala Leu Glu Asn Asp Val Ser Asn Gly Trp Asp Pro Asn Asp Met
385                 390                 395                 400

Phe Arg Tyr Asn Glu Glu Asn Tyr Gly Val Val Ser Thr Tyr Asp Ser
                405                 410                 415

Ser Leu Ser Ser Tyr Thr Val Pro Leu Glu Arg Asp Asn Ser Glu Glu
            420                 425                 430

Phe Leu Lys Arg Glu Ala Arg Ala Asn Gln Leu Ala Glu Glu Ile Glu
        435                 440                 445

Ser Ser Ala Gln Tyr Lys Ala Arg Val Ala Leu Glu Asn Asp Asp Arg
450                 455                 460

Ser Glu Glu Glu Lys Tyr Thr Ala Val Gln Arg Asn Ser Ser Glu Arg
465                 470                 475                 480
```

-continued

```
Glu Gly His Ser Ile Asn Thr Arg Glu Asn Lys Tyr Ile Pro Pro Gly
                485                 490                 495

Gln Arg Asn Arg Glu Val Ile Ser Trp Gly Ser Gly Arg Gln Asn Ser
            500                 505                 510

Pro Arg Met Gly Gln Pro Gly Ser Gly Ser Met Pro Ser Arg Ser Thr
            515                 520                 525

Ser His Thr Ser Asp Phe Asn Pro Asn Ser Gly Ser Asp Gln Arg Val
            530                 535                 540

Val Asn Gly Gly Val Pro Trp Pro Ser Pro Cys Pro Ser Pro Ser Ser
545                 550                 555                 560

Arg Pro Pro Ser Arg Tyr Gln Ser Gly Pro Asn Ser Leu Pro Pro Arg
                565                 570                 575

Ala Ala Thr Pro Thr Arg Pro Pro Ser Arg Pro Ser Arg Pro Ser
            580                 585                 590

Arg Pro Pro Ser His Pro Ser Ala His Gly Ser Pro Ala Pro Val Ser
            595                 600                 605

Thr Met Pro Lys Arg Met Ser Ser Glu Gly Pro Pro Arg Met Ser Pro
            610                 615                 620

Lys Ala Gln Arg His Pro Arg Asn His Arg Val Ser Ala Gly Arg Gly
625                 630                 635                 640

Ser Ile Ser Ser Gly Leu Glu Phe Val Ser His Asn Pro Pro Ser Glu
                645                 650                 655

Ala Ala Thr Pro Pro Val Ala Arg Thr Ser Pro Ser Gly Gly Thr Trp
            660                 665                 670

Ser Ser Val Val Ser Gly Val Pro Arg Leu Ser Pro Lys Thr His Arg
            675                 680                 685

Pro Arg Ser Pro Arg Gln Asn Ser Ile Gly Asn Thr Pro Ser Gly Pro
            690                 695                 700

Val Leu Ala Ser Pro Gln Ala Gly Ile Ile Pro Thr Glu Ala Val Ala
705                 710                 715                 720

Met Pro Ile Pro Ala Ala Ser Pro Thr Pro Ala Ser Pro Ala Ser Asn
                725                 730                 735

Arg Ala Val Thr Pro Ser Ser Glu Ala Lys Asp Ser Arg Leu Gln Asp
            740                 745                 750

Gln Arg Gln Asn Ser Pro Ala Gly Asn Lys Glu Asn Ile Lys Pro Asn
            755                 760                 765

Glu Thr Ser Pro Ser Phe Ser Lys Ala Glu Asn Lys Gly Ile Ser Pro
    770                 775                 780

Val Val Ser Glu His Arg Lys Gln Ile Asp Asp Leu Lys Lys Phe Lys
785                 790                 795                 800

Asn Asp Phe Arg Leu Gln Pro Ser Ser Thr Ser Glu Ser Met Asp Gln
                805                 810                 815

Leu Leu Asn Lys Asn Arg Glu Gly Glu Lys Ser Arg Asp Leu Ile Lys
            820                 825                 830

Asp Lys Ile Glu Pro Ser Ala Lys Asp Ser Phe Ile Glu Asn Ser Ser
            835                 840                 845

Ser Asn Cys Thr Ser Gly Ser Ser Lys Pro Asn Ser Pro Ser Ile Ser
            850                 855                 860

Pro Ser Ile Leu Ser Asn Thr Glu His Lys Arg Gly Pro Glu Val Thr
865                 870                 875                 880

Ser Gln Gly Val Gln Thr Ser Ser Pro Ala Cys Lys Gln Glu Lys Asp
                885                 890                 895

Asp Lys Glu Glu Lys Lys Asp Ala Ala Glu Gln Val Arg Lys Ser Thr
```

```
                    900                 905                 910

Leu Asn Pro Asn Ala Lys Glu Phe Asn Pro Arg Ser Phe Ser Gln Pro
        915                 920                 925

Lys Pro Ser Thr Thr Pro Thr Ser Pro Arg Pro Gln Ala Gln Pro Ser
    930                 935                 940

Pro Ser Met Val Gly His Gln Gln Pro Thr Pro Val Tyr Thr Gln Pro
945                 950                 955                 960

Val Cys Phe Ala Pro Asn Met Met Tyr Pro Val Pro Val Ser Pro Gly
                965                 970                 975

Val Gln Pro Leu Tyr Pro Ile Pro Met Thr Pro Met Pro Val Asn Gln
            980                 985                 990

Ala Lys Thr Tyr Arg Ala Val Pro Asn Met Pro Gln Gln Arg Gln Asp
        995                 1000                1005

Gln His His Gln Ser Ala Met Met His Pro Ala Ser Ala Ala Gly Pro
    1010                1015                1020

Pro Ile Ala Ala Thr Pro Pro Ala Tyr Ser Thr Gln Tyr Val Ala Tyr
1025                1030                1035                1040

Ser Pro Gln Gln Phe Pro Asn Gln Pro Leu Val Gln His Val Pro His
                1045                1050                1055

Tyr Gln Ser Gln His Pro His Val Tyr Ser Pro Val Ile Gln Gly Asn
            1060                1065                1070

Ala Arg Met Met Ala Pro Pro Thr His Ala Gln Pro Gly Leu Val Ser
        1075                1080                1085

Ser Ser Ala Thr Gln Tyr Gly Ala His Glu Gln Thr His Ala Met Tyr
    1090                1095                1100

Ala Cys Pro Lys Leu Pro Tyr Asn Lys Glu Thr Ser Pro Ser Phe Tyr
1105                1110                1115                1120

Phe Ala Ile Ser Thr Gly Ser Leu Ala Gln Gln Tyr Ala His Pro Asn
                1125                1130                1135

Ala Thr Leu His Pro His Thr Pro His Pro Gln Pro Ser Ala Thr Pro
            1140                1145                1150

Thr Gly Gln Gln Gln Ser Gln His Gly Gly Ser His Pro Ala Pro Ser
        1155                1160                1165

Pro Val Gln His His Gln His Gln Ala Ala Gln Ala Leu His Leu Ala
    1170                1175                1180

Ser Pro Gln Gln Gln Ser Ala Ile Tyr His Ala Gly Leu Ala Pro Thr
1185                1190                1195                1200

Pro Pro Ser Met Thr Pro Ala Ser Asn Thr Gln Ser Pro Gln Asn Ser
                1205                1210                1215

Phe Pro Ala Ala Gln Gln Thr Val Phe Thr Ile His Pro Ser His Val
            1220                1225                1230

Gln Pro Ala Tyr Thr Asn Pro Pro His Met Ala His Val Pro Gln Ala
        1235                1240                1245

His Val Gln Ser Gly Met Val Pro Ser His Pro Thr Ala His Ala Pro
    1250                1255                1260

Met Met Leu Met Thr Thr Gln Pro Pro Gly Gly Pro Gln Ala Ala Leu
1265                1270                1275                1280

Ala Gln Ser Ala Leu Gln Pro Ile Pro Val Ser Thr Thr Ala His Phe
                1285                1290                1295

Pro Tyr Met Thr His Pro Ser Val Gln Ala His His Gln Gln Gln Leu
            1300                1305                1310

<210> SEQ ID NO 7
```

```
<211> LENGTH: 19
<212> TYPE: DNA
<213> ORGANISM: Artificial Sequence
<220> FEATURE:
<223> OTHER INFORMATION: primer

<400> SEQUENCE: 7
gacccgagaa accaccagt                                                    19

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
agaggcaacg aattaggatg t                                                 21

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
ccagagggag gcacagtagt                                                   20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ttaaaacgga gaggcagatg                                                   20

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
gcttgggtgg agaggctatt c                                                 21

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
caaggtgaga tgacaggaga tc                                                22
```